(12) United States Patent
Cao et al.

(10) Patent No.: US 11,454,731 B2
(45) Date of Patent: Sep. 27, 2022

(54) IMAGE SENSORS HAVING RADIATION DETECTORS AND MASKS

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 17/236,553

(22) Filed: Apr. 21, 2021

(65) Prior Publication Data

US 2021/0239861 A1 Aug. 5, 2021

Related U.S. Application Data

(63) Continuation of application No. PCT/CN2018/114121, filed on Nov. 6, 2018.

(51) Int. Cl.
*G01T 1/29* (2006.01)

(52) U.S. Cl.
CPC ................................ *G01T 1/295* (2013.01)

(58) Field of Classification Search
CPC .. G01T 1/295; G01T 1/16; A61B 6/03; A61B 6/06; A61B 6/42; A61B 6/4266; A61B 6/4435; A61B 6/5241; A61B 6/547; G01N 23/04; G01N 2223/40; G01N 2223/501; G01V 5/0066
USPC .................................................... 250/370.08
See application file for complete search history.

(56) References Cited

U.S. PATENT DOCUMENTS

| | | | | |
|---|---|---|---|---|
| 4,725,891 A | * | 2/1988 | Manian | H04N 1/0891 358/406 |
| 5,847,398 A | | 12/1998 | Shahar et al. | |
| 5,864,146 A | | 1/1999 | Karellas | |
| 2012/0106697 A1 | * | 5/2012 | Carton | G03B 42/02 382/132 |
| 2013/0202087 A1 | | 8/2013 | Cox | |

FOREIGN PATENT DOCUMENTS

| | | |
|---|---|---|
| CN | 101622552 A | 1/2010 |
| CN | 107533146 A | 1/2018 |
| WO | 2018053778 A1 | 3/2018 |
| WO | 2018112721 A1 | 6/2018 |

* cited by examiner

*Primary Examiner* — David P Porta
*Assistant Examiner* — Gisselle M Gutierrez
(74) *Attorney, Agent, or Firm* — Ipro, PLLC; Qian Gu

(57) ABSTRACT

Disclosed herein is an image sensor comprising: a plurality of radiation detectors; a mask with a plurality of radiation transmitting zones and a radiation blocking zone; and an actuator configured to move the plurality of radiation detectors from a first position to a second position and to move the mask from a third position to a fourth position; wherein while the radiation detectors are at the first position and the mask is at the third position and while the radiation detectors are at the second position and the mask is at the fourth position, the radiation blocking zone blocks radiation from a radiation source that would otherwise incident on a dead zone of the image sensor and the radiation transmitting zones allow at least a portion of radiation from the radiation source that would incident on active areas of the image sensor to pass through.

30 Claims, 22 Drawing Sheets

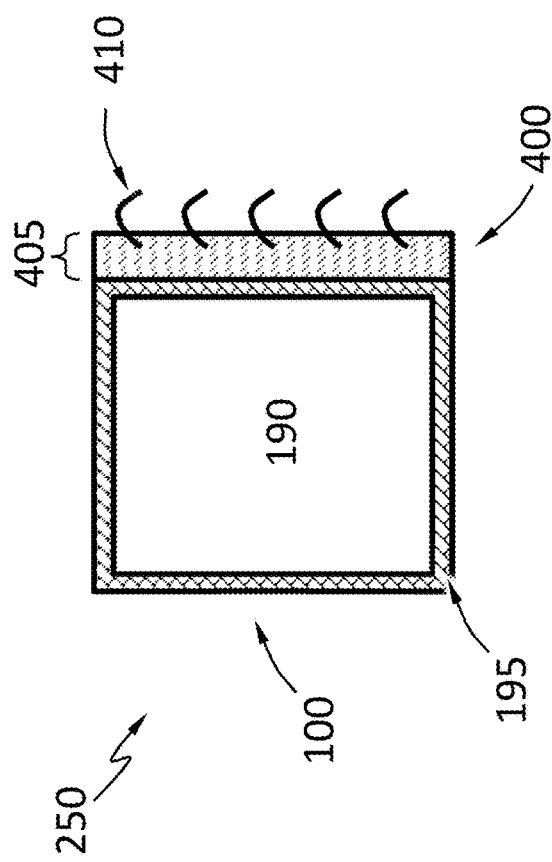
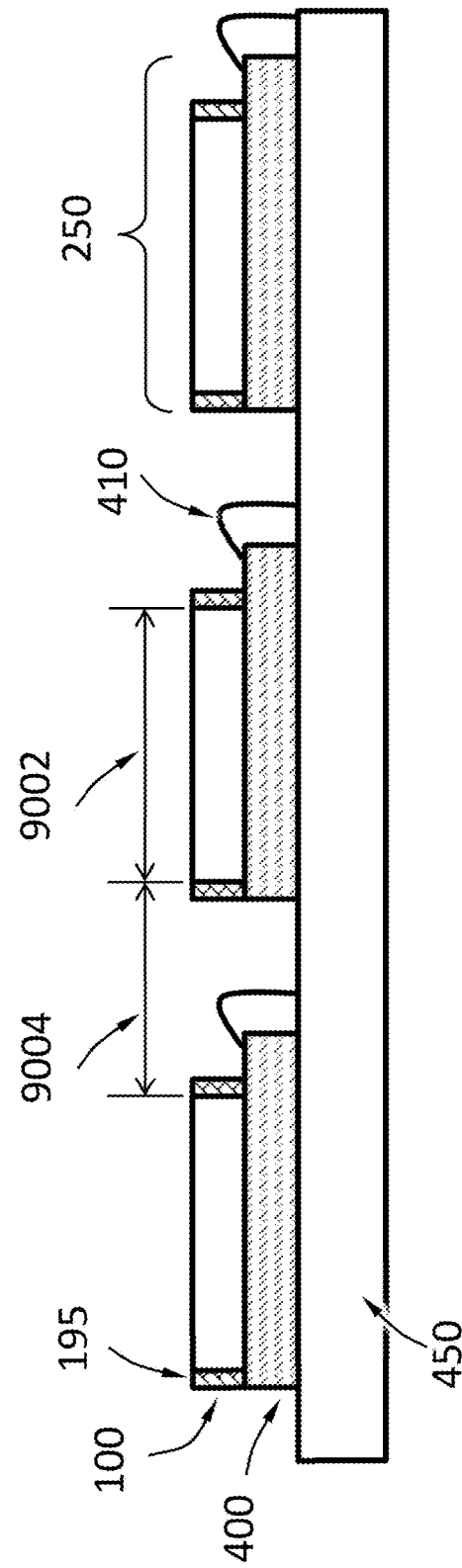

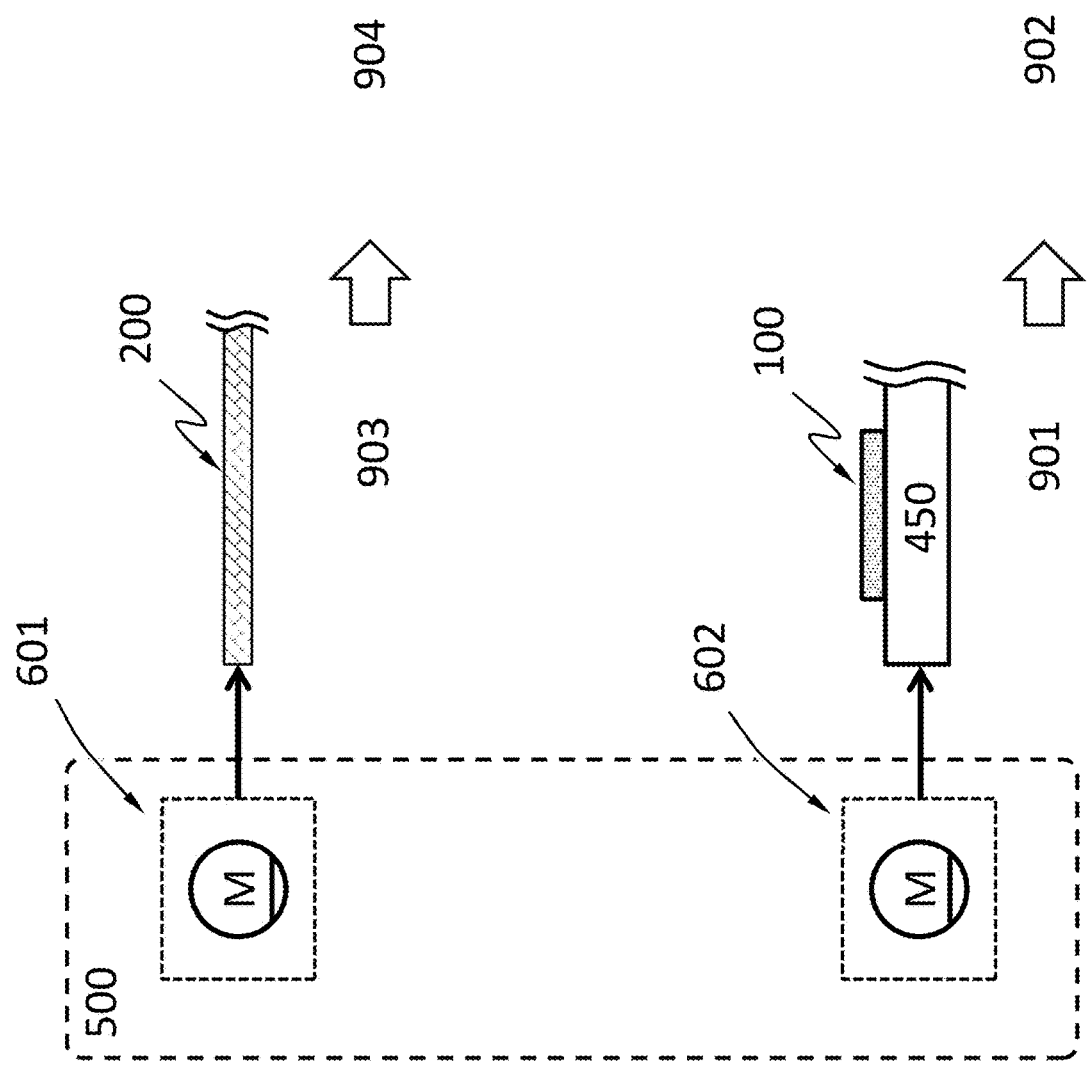

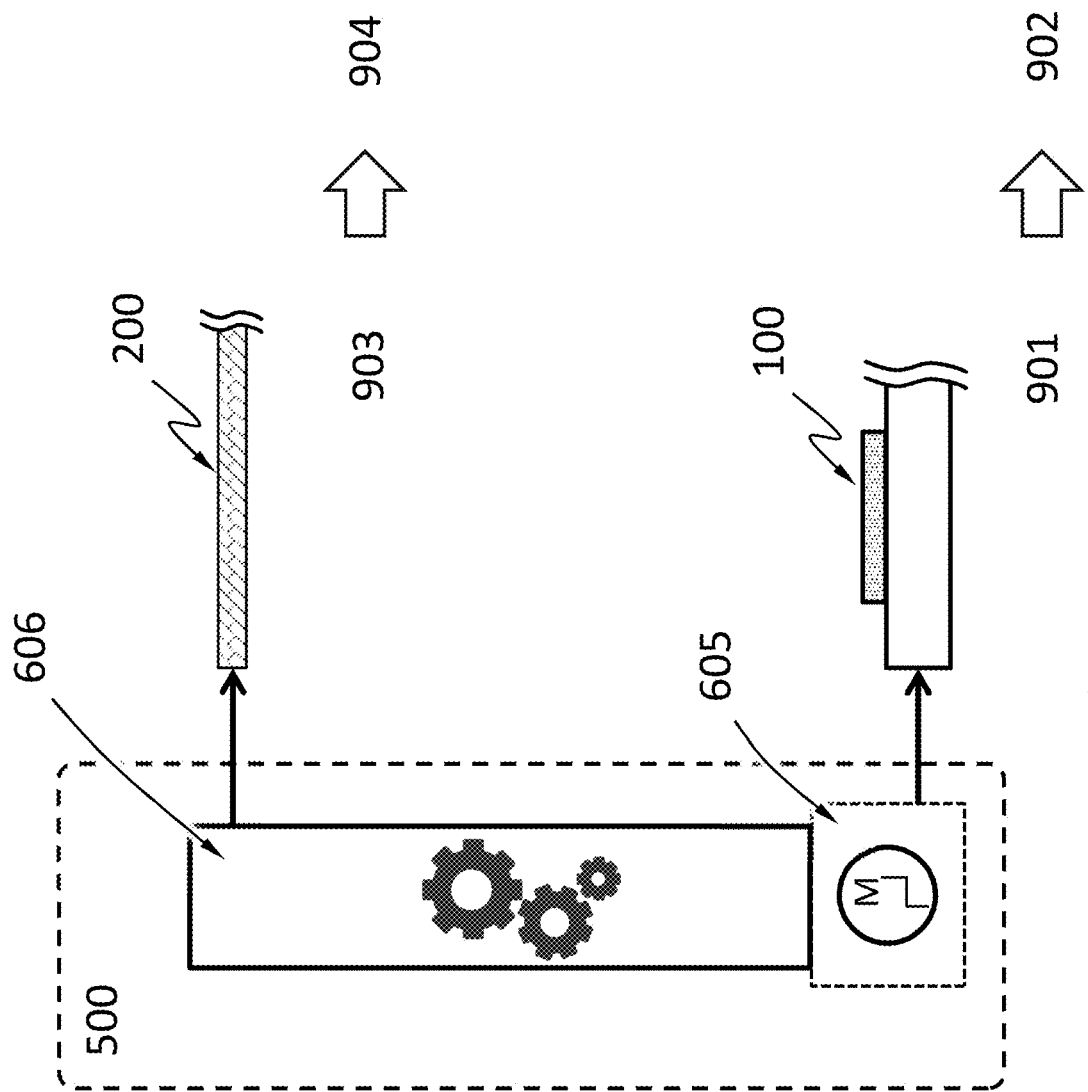

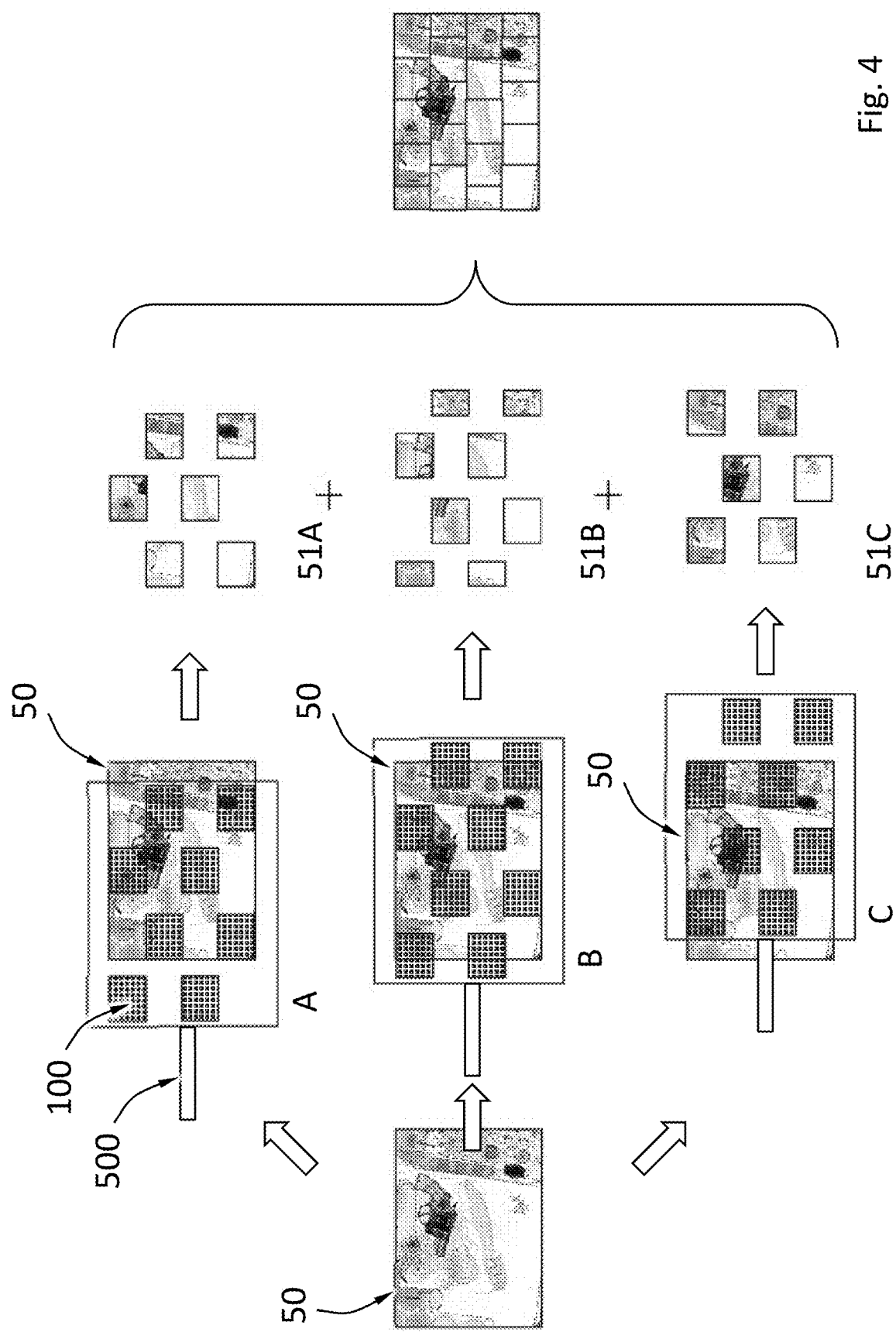

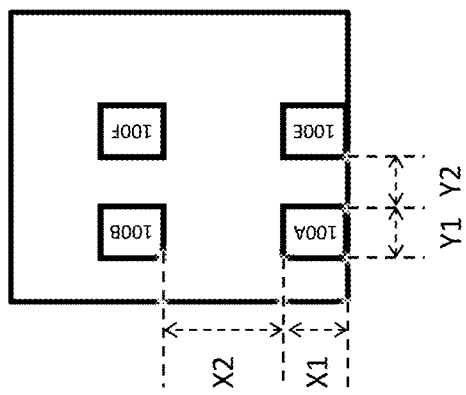
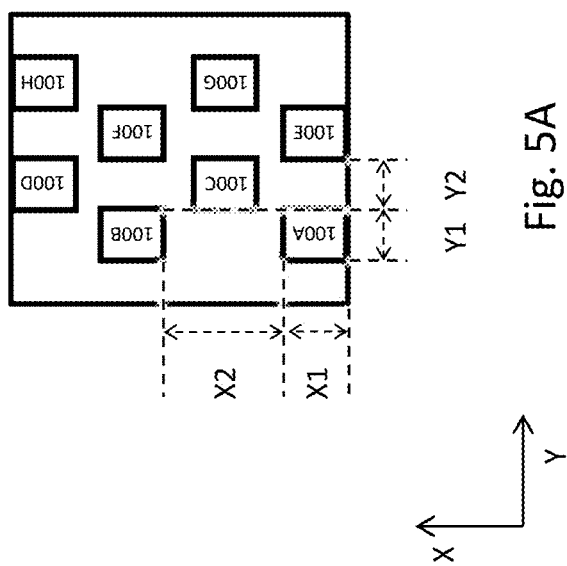
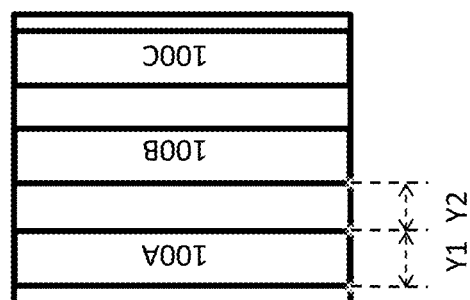
Fig. 5A
Fig. 5B
Fig. 5C

IMAGE SENSORS HAVING RADIATION DETECTORS AND MASKS

BACKGROUND

Radiation detectors may be devices used to measure the flux, spatial distribution, spectrum or other properties of radiations.

Radiation detectors may be used for many applications. One important application is imaging. Radiation imaging is a radiography technique and can be used to reveal the internal structure of a non-uniformly composed and opaque object such as the human body.

Early radiation detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to radiation, electrons excited by radiation are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of radiation detectors are radiation image intensifiers. Components of a radiation image intensifier are usually sealed in a vacuum. In contrast to photographic plates, photographic films, and PSP plates, radiation image intensifiers may produce real-time images, i.e., do not require post-exposure processing to produce images. Radiation first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident radiation. The emitted electrons are projected, through electron optics, onto an output phosphor and cause the output phosphor to produce a visible-light image.

Scintillators operate somewhat similarly to radiation image intensifiers in that scintillators (e.g., sodium iodide) absorb radiation and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of radiation. A scintillator thus has to strike a compromise between absorption efficiency and resolution.

Semiconductor radiation detectors largely overcome this problem by direct conversion of radiation into electric signals. A semiconductor radiation detector may include a semiconductor layer that absorbs radiation in wavelengths of interest. When a particle of radiation is absorbed in the semiconductor layer, multiple charge carriers (e.g., electrons and holes) are generated and swept under an electric field towards electrical contacts on the semiconductor layer.

SUMMARY

Disclosed herein is an image sensor comprising: a plurality of radiation detectors; a mask with a plurality of radiation transmitting zones and a radiation blocking zone; and an actuator configured to move the plurality of radiation detectors from a first position to a second position and to move the mask from a third position to a fourth position; wherein while the radiation detectors are at the first position and the mask is at the third position and while the radiation detectors are at the second position and the mask is at the fourth position, the radiation blocking zone blocks radiation from a radiation source that would otherwise incident on a dead zone of the image sensor and the radiation transmitting zones allow at least a portion of radiation from the radiation source that would incident on active areas of the image sensor to pass through.

According to an embodiment, the image sensor is configured to capture, by using the radiation detectors, an image of a first portion of a scene when the radiation detectors are at the first position and the image sensor is configure to capture, by using the radiation detectors, an image of a second portion of a scene when the radiation detectors are at the second position, wherein the image sensor is configured to form an image of the scene by stitching the image of the first portion and the image of the second portion.

According to an embodiment, the plurality of radiation detectors are spaced apart.

According to an embodiment, the image sensor further comprises a shutter configured to block the radiation from the radiation source during movement of the radiation detectors.

According to an embodiment, the actuator comprises a first linear motor and a second linear motor; wherein the first linear motor is configured to move the radiation detectors from the first position to the second position; wherein the second linear motor is configured to move the mask from the third position to the fourth position.

According to an embodiment, the actuator comprises a third linear motor and a linkage; wherein the third linear motor is configured to move radiation detectors from the first position to the second position; wherein the linkage couples the mask to the radiation detectors such that movement of the radiation detectors from the first position to the second position causes the mask to move from the third position to the fourth position.

According to an embodiment, the actuator comprises a third linear motor and a linkage; the third linear motor is configured to move the mask move from the third position to the fourth position; wherein the linkage couples the radiation detectors to the mask such that movement of the mask from the third position to the fourth position causes the radiation detectors to move from the first position to the second position.

According to an embodiment, the actuator comprises a third linear motor and a linkage; wherein the third linear motor is configured to drive the linkage; wherein the linkage causes the mask to move from the third position to the fourth position and causes the radiation detectors to move from the first position to the second position.

According to an embodiment, the actuator comprises a step motor and a transmission; wherein the step motor is configured to move radiation detectors from the first position to the second position and to drive the transmission; wherein the transmission is configured to move the mask from the third position to the fourth position.

According to an embodiment, at least some of the plurality of radiation detectors are arranged in staggered rows.

According to an embodiment, radiation detectors in a same row are uniform in size; wherein a distance between two neighboring radiation detectors in a same row is greater than a width of one radiation detector in the same row in an extending direction of the row and is less than twice that width.

According to an embodiment, active areas of the radiation detectors tessellate the scene at the positions.

According to an embodiment, at least some of the plurality of radiation detectors comprise multiple layers of detectors.

According to an embodiment, at least some of the plurality of radiation detectors are rectangular in shape.

According to an embodiment, at least some of the plurality of radiation detectors are hexagonal in shape.

According to an embodiment, at least one of the plurality of radiation detectors comprises a radiation absorption layer and an electronics layer; wherein the radiation absorption layer comprises an electrode; wherein the electronics layer comprises an electronics system; wherein the electronics system comprises: a first voltage comparator configured to compare a voltage of the electrode to a first threshold, a second voltage comparator configured to compare the voltage to a second threshold, a counter configured to register a number of particles of radiation reaching the radiation absorption layer, and a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, if the second voltage comparator determines that an absolute value of the voltage equals or exceeds an absolute value of the second threshold.

According to an embodiment, the electronics system further comprises a capacitor module electrically connected to the electrode, wherein the capacitor module is configured to collect charge carriers from the electrode.

According to an embodiment, the controller is configured to activate the second voltage comparator at a beginning or expiration of the time delay.

According to an embodiment, the electronics system further comprises a voltmeter, wherein the controller is configured to cause the voltmeter to measure the voltage upon expiration of the time delay.

According to an embodiment, the controller is configured to determine energy of a particle of radiation based on a value of the voltage measured upon expiration of the time delay.

According to an embodiment, the controller is configured to connect the electrode to an electrical ground.

According to an embodiment, a rate of change of the voltage is substantially zero at expiration of the time delay.

According to an embodiment, a rate of change of the voltage is substantially non-zero at expiration of the time delay.

Disclosed herein is a system comprising the image sensor described herein and a radiation source, wherein the system is configured to perform radiography on human chest or abdomen.

Disclosed herein is a system comprising the image sensor described herein and a radiation source, wherein the system is configured to perform radiography on human mouth.

Disclosed herein is a cargo scanning or non-intrusive inspection (NII) system, comprising the image sensor described herein and a radiation source, wherein the cargo scanning or non-intrusive inspection (NII) system is configured to form an image using radiation transmitted through an object inspected.

Disclosed herein is a full-body scanner system comprising the image sensor described herein and a radiation source.

Disclosed herein is a radiation computed tomography (radiation CT) system comprising the image sensor described herein and a radiation source.

Disclosed herein is an electron microscope comprising the image sensor described herein, an electron source and an electronic optical system.

Disclosed herein is a system comprising the image sensor described herein, wherein the system is a radiation telescope, or a radiation microscopy, or wherein the system is configured to perform mammography, industrial defect detection, microradiography, casting inspection, weld inspection, or digital subtraction angiography.

BRIEF DESCRIPTION OF FIGURES

FIG. 2A schematically shows a top view of a package including the detector and a printed circuit board (PCB), according to an embodiment.

FIG. 2B schematically shows a cross-sectional view of the image sensor with a plurality of the packages of FIG. 2A, according to an embodiment.

FIG. 3A-FIG. 3C schematically show examples of suitable designs of an actuator, according to an embodiment.

FIG. 4 schematically shows an image sensor taking a series of images of a scene, according to an embodiment.

FIG. 5A-5C schematically show arrangements of the radiation detectors in an image sensor, according to some embodiments.

DETAILED DESCRIPTION

Figure 1A:
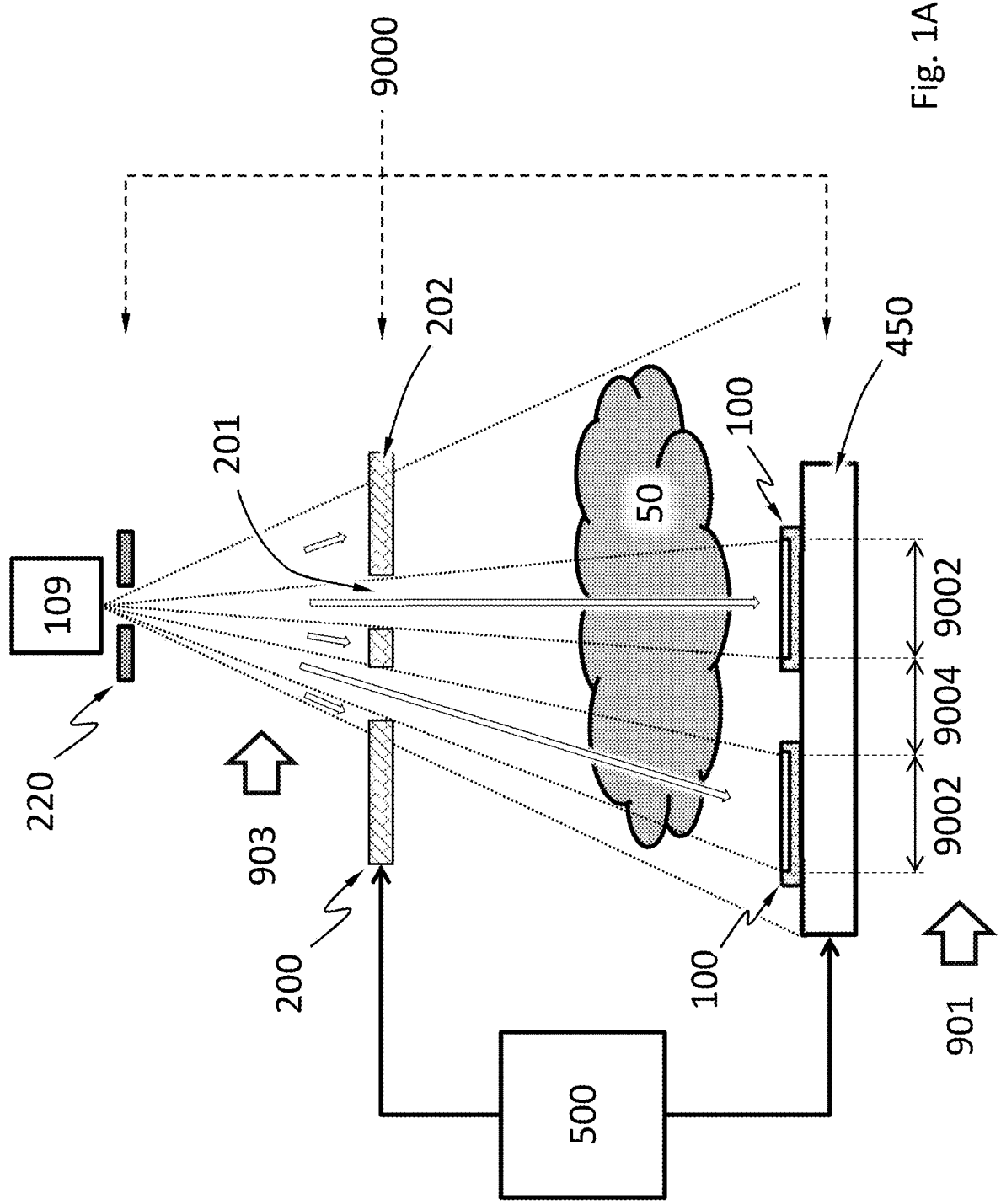
FIG. 1A and FIG. 1B schematically show an image sensor, according to an embodiment.
Figure 1B:
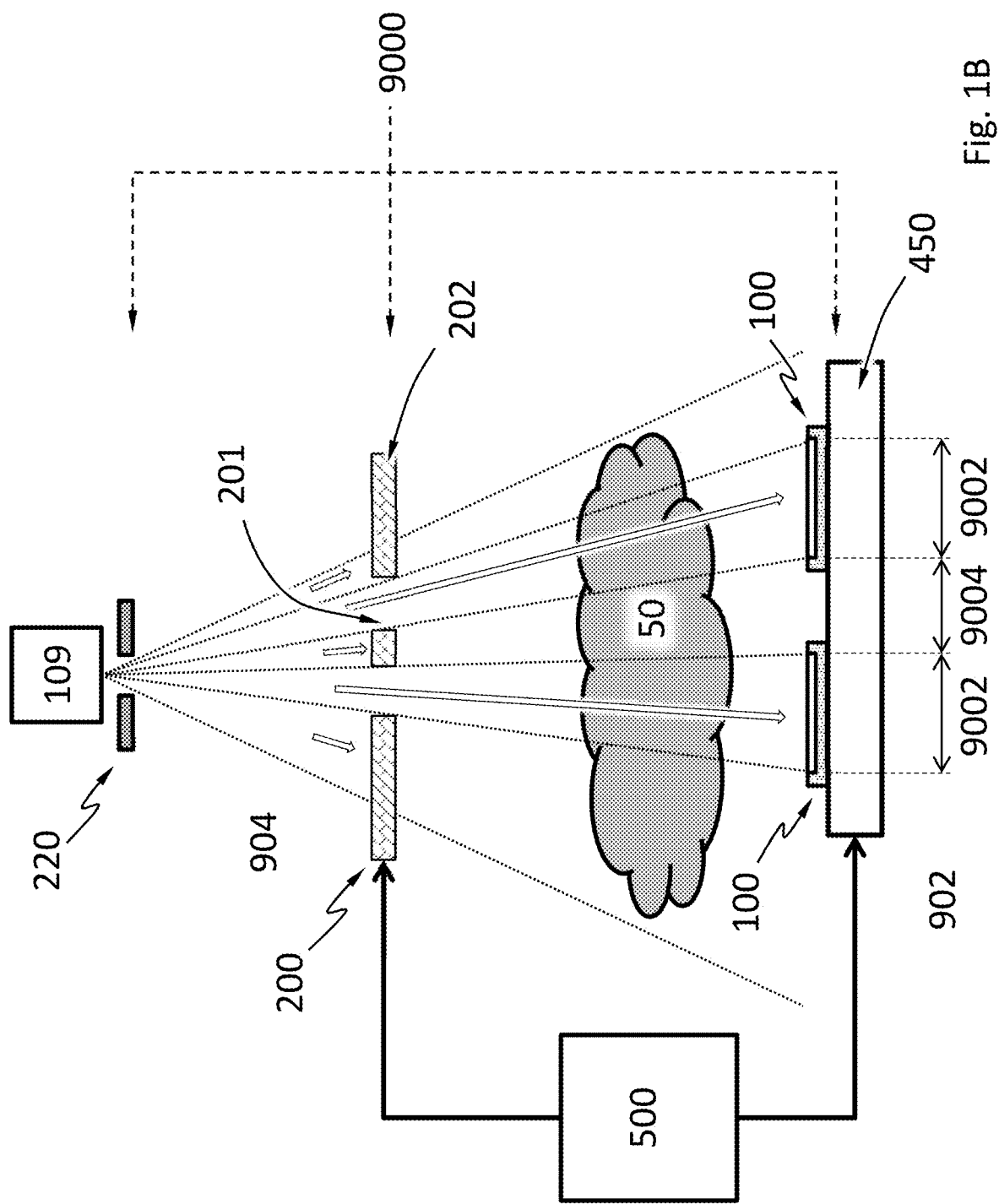

FIG. 1A and FIG. 1B schematically show an image sensor 9000, according to an embodiment. The image sensor 9000 may take images of different portions of a scene 50 while the image sensor 9000 is at different positions (e.g., positions 901 and 902) relative to the scene 50. The image sensor 9000 includes a plurality of radiation detectors 100, a mask 200, and an actuator 500. The plurality of radiation detectors 100 may be configured to receive radiation from a radiation source 109 and through a portion of the scene 50. The radiation detectors 100 of the image sensor 9000 may be in one or more packages 250 that are mounted to a system printed circuit board (PCB) 450.

FIG. 2A schematically shows a top view of one of packages 250 including one or more of the radiation detectors 100 and a PCB 400, according to an embodiment. The term "PCB" as used herein is not limited to a particular material. For example, a PCB may include a semiconductor. The radiation detectors 100 in this package 250 are mounted to the PCB 400. The wiring between the radiation detectors 100 and the PCB 400 is not shown for the sake of clarity. The PCB 400 may have an area not covered by the radiation detectors 100 (e.g., for accommodating bonding wires 410). The radiation detectors 100 may each have an active area 190. The active area 190 is sensitive to radiation. Radiation incident on the active area 190 may be detected by the radiation detectors 100. The radiation detectors 100 may each have a perimeter zone 195 near the edges thereof. The perimeter zone 195 is not sensitive to incident radiation and the detectors 100 do not detect radiation incident on the perimeter zone 195.

FIG. 2B schematically shows a cross-sectional view several packages 250 of the image sensor 9000, according to an embodiment. The electrical connection between the PCBs 400 in the packages 250 and the system PCB 450 may be made by bonding wires 410. The PCB 400 may have an area 405 not covered by the radiation detectors 100 of the packages 250, for example, to accommodate the bonding wires 410 on the PCB 400. In an example, the packages 250 have gaps in between to accommodate the bonding wires 410 on the system PCB 450. The gaps may be approximately 1 mm or more. Radiation incident on the perimeter zones 195, on the area 405 or on the gaps cannot be detected by the radiation detectors 100 of the image sensor 9000. A dead zone of a radiation detector is the area of the radiation-receiving surface of the radiation detector, in which incident radiation cannot be detected by the radiation detector. A dead zone of a package (e.g., package 250) is the area of the radiation-receiving surface of the package, in which incident radiation cannot be detected by the radiation detector or radiation detectors in the package. In this example shown in FIG. 2A, the dead zone of the package 250 includes the perimeter zones 195 and the area 405. A dead zone (e.g., 9004) of the image sensor 9000 with a group of packages (e.g., packages mounted on the same PCB, packages arranged in the same layer) includes the combination of the dead zones of the packages in the group and the gaps among the packages. An active area 9002 of the image sensor 9000 is the combination of the active areas 190 of the radiation detectors 100 in the image sensor 9000.

As schematically shown in FIG. 1A and FIG. 1B, the mask 200 has a plurality of radiation transmitting zones 201 and a radiation blocking zone 202. The radiation blocking zone 202 prevents the radiation incident thereon from passing through, and the radiation transmitting zones 201 allow at least a portion of the radiation incident thereon to pass through. The radiation blocking zone 202 may be aligned with the dead zone 9004 of the image sensor 9000. The radiation blocking zone 202 may block radiation from a radiation source (e.g., radiation source 109) that would otherwise reach the dead zone 9004. For example, the radiation blocking zone 202 is configured to prevent radiation from the radiation source 109 that otherwise would reach the dead zone 9004 from reaching the scene 50. The radiation transmitting zones 201 may be aligned with the active area 9002 of the image sensor 9000. The radiation transmitting zones 201 may allow at least a portion of radiation from a radiation source (e.g., radiation source 109) to reach the active area 9002. The positions of the radiation transmitting zones 201 and the radiation blocking zone 202 may be fixed relative to the mask 200. One example of the mask 200 may be a metal sheet with a thickness enough for blocking radiation with holes therein. The holes may be the radiation transmitting zones 201 and the rest of the metal sheet may be the radiation blocking zone 202.

The actuator 500, as shown in FIG. 1A and FIG. 1B, is configured to move the radiation detectors 100 and the mask 200 to a plurality of positions. The actuator 500 may have one or multiple drivers (e.g., electric motors). When the actuator 500 may move the radiation detectors 100 and the mask 200 without relative movement. The actuator 500 may move the radiation detectors 100 and the mask 200 relative to each other. In the example shown in FIG. 1A, the radiation detectors 100 are at a first position 901, and the mask 200 is at a third position 903. In the example shown in FIG. 1B, the actuator 500 moves the radiation detectors 100 from the first position 901 to a second position 902 and moves the mask 200 from the third position 903 to a fourth position 904. At each of the positions, the image sensor 9000 takes an image of a portion of the scene 50. Namely, an image of a first portion of the scene 50 is captured by the image sensor 9000 by using the radiation detectors 100 when the radiation detectors 100 are at the first position 901 and an image of a second portion of the scene 50 is captured by the image sensor 9000 when the radiation detectors 100 are at the second position 902. The images of the portions may be then stitched to form an image of the scene 50. The images of the portions may have overlap among one another to facilitate stitching.

According to one embodiment, while the radiation detectors 100 are at the first position 901 and the mask 200 is at the third position 903 and while the radiation detectors 100 are at the second position 902 and the mask 200 is at the fourth position 904, the radiation blocking zone 202 blocks radiation from the radiation source 109 that would otherwise incident on the dead zone 9004 of the image sensor 9000 and the radiation transmitting zones 201 allow at least a portions of radiation from the radiation source 109 that would incident on the active areas 9002 of the image sensor 9000 to pass through.

The actuator 500 may be positioned between the scene and the radiation source 109, between the scene 50 and the image sensor 9000, or at another suitable position. The actuator 500 may be configured to move the mask 200 and the radiation detectors 100 among multiple positions at which the image sensor 9000 captures images of the portions of the scene 50, such that the alignment between the radiation detectors 100 with the mask 200 is maintained at each of these positions.

Figure 3B:
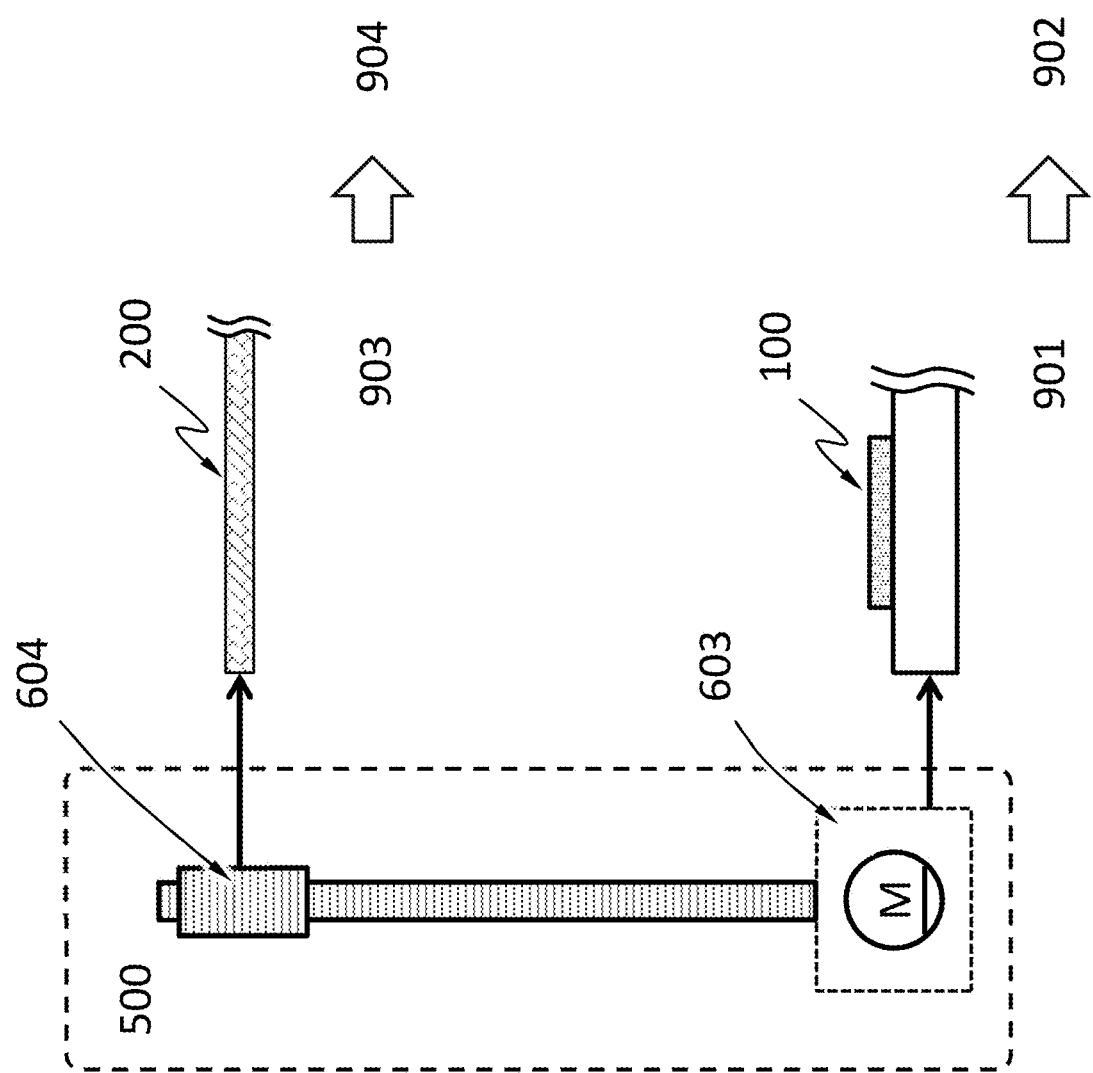

The actuator 500 may have any suitable designs, examples of which are schematically shown in FIG. 3A-FIG. 3C. According to an embodiment, the actuator 500 may comprise a first linear motor 601 and a second linear motor 602, which may engage the mask 200 and the radiation detectors 100 respectively, as shown in FIG. 3A. The first linear motor 601 is configured to move the radiation detectors 100, for example, from the first position 901 to the second position 902. The second linear motor 602 is configured to move the mask 200, for example, from the third position 903 to the fourth position 904.

According to one embodiment, the actuator 500 may comprise a third linear motor 603 and a linkage 604, which may engage the radiation detectors 100 and the mask 200 respectively, or vice versa, as shown in FIG. 3B. In the example shown, the third linear motor 603 is configured to move the radiation detectors 100, for example, from the first position 901 to the second position 902, and the linkage 604 couples the mask 200 to the radiation detectors 100 such that movement of the radiation detectors 100 from the first position 901 to the second position 902 causes the mask 200 to move from the third position 903 to the fourth position 904. In another example, the third linear motor 603 is configured to move the mask 200, for example, from the third position 903 to the fourth position 904, and the linkage 604 couples the radiation detectors 100 to the mask 200 such that movement of the mask 200 from the third position 903 to the fourth position 904 causes the radiation detectors 100 to move from the first position 901 to the second position 902. In yet another example, the third linear motor 603 may drive the linkage 604 and the linkage 604 drives the mask 200 and the radiation detectors 100. For example, the linkage 604 causes the mask 200 to move from the third position 903 to the fourth position 904 and causes the radiation detectors 100 to move from the first position 901 to the second position 902.

According to one embodiment, the actuator 500 may comprise a step motor 605 and a transmission 606, which may engage the radiation detectors 100 and the mask 200 respectively, or vice versa, as shown in FIG. 3C. In the example shown, the step motor 605 is configured to move the radiation detectors 100, for example, from the first position 901 to the second position 902. The step motor 605 is also configured to drive the transmission 606 and the transmission 606 is configured to move the mask 200, for example, from the third position 903 to the fourth position 904. The transmission 606 may cause a displacement of the mask 200 at a magnitude of a displacement of the step motor 605 multiplied by a gear ratio of the transmission 606.

As schematically shown in FIG. 1A and FIG. 1B, the image sensor 9000 may include a shutter 220. The shutter 220 is configured to block the radiation from the radiation source 109 during movements of the radiation detectors 100 and the mask 200.

As shown in FIG. 4, according to an embodiment, at least some of the radiation detectors 100 of the image sensor 9000 are arranged in an array. To form an image of the scene 50, the actuator 500 moves the radiation detectors 100 to multiple positions (e.g., A, B and C in FIG. 4) relative to the scene 50, where the image sensor 9000 captures images (e.g., 51A, 51B and 51C) of portions of the scene 50 at these positions, respectively. Every point of the scene 50 is in at least one image of a portion. Namely, the images of the portions when stitched together cover the entire scene 50. The images of the portions may have overlaps among them to facilitate stitching.

The radiation detectors 100 may be arranged in a variety of ways in the image sensor 9000. FIG. 5A schematically shows one arrangement, according to an embodiment, where at least some of the radiation detectors 100 are arranged in staggered rows. For example, detectors 100A and 100B are in the same row, aligned in the Y direction, and uniform in size; detectors 100C and 100D are in the same row, aligned in the Y direction, and uniform in size. Radiation detectors 100A and 100B are staggered in the X direction with respect to radiation detectors 100C and 100D. According to an embodiment, a distance X2 between two neighboring radiation detectors 100A and 100B in the same row is greater than a width X1 (i.e., dimension in the X direction, which is the extending direction of the row) of one radiation detector in the same row and is less than twice the width X1. Radiation detectors 100A and 100E are in a same column, aligned in the X direction, and uniform in size; a distance Y2 between two neighboring radiation detectors 100A and 100E in the same column is less than a width Y1 (i.e., dimension in the Y direction) of one radiation detector in the same column. This arrangement allows imaging of the scene as shown in FIG. 4, and an image of the scene may be obtaining from stitching three images of portions of the scene captured at three positions spaced apart in the X direction.

FIG. 5B schematically shows another arrangement, according to an embodiment, where the radiation detectors 100 are arranged in a rectangular grid. For example, the detectors 100 may include detectors 100A, 100B, 100E and 100F as arranged exactly in FIG. 5A, without detectors 100C, 100D, 100G, or 100H in FIG. 5A. This arrangement allows imaging of the scene by taking images of portions of the scene at six positions. For example, three positions spaced apart in the X direction and another three positions spaced apart in the X direction and spaced apart in the Y direction from the first three positions.

Other arrangements may also be possible. For example, in FIG. 5C, the detectors 100 may span the whole width of the image sensor 9000 in the X-direction, with a distance Y2 between two neighboring detectors 100 being less than a width of one radiation detector Y1. Assuming the width of the detectors in the X direction is greater than the width of the scene in the X direction, the image of the scene may be stitched from two images of portions of the scene captured at two positions spaced apart in the Y direction. The radiation detectors 100 may be arranged in multiple layers, where at least some of the plurality of radiation detectors 100 are arranged such that radiation incident on the dead zone 9004 of one layer is captured by the radiation detectors in another layer.

Figure 6:
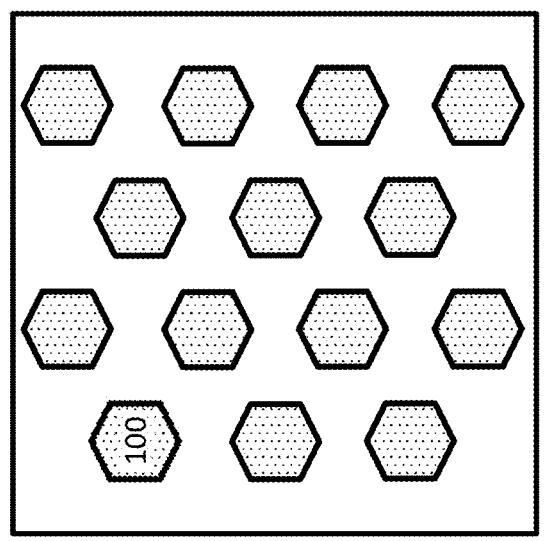
FIG. 6 schematically shows an image sensor with plurality of detectors that are hexagonal in shape, according to an embodiment.

The radiation detectors describe above may be provided with any suitable size and shapes. According to an embodiment (e.g., in FIG. 4), at least some of the radiation detectors are rectangular in shape. According to an embodiment, as shown in FIG. 6, at least some of the radiation detectors are hexagonal in shape. In such radiation detectors, the radiation detectors and the corresponding masks that are aligned may have the same shape.

Figure 7A:
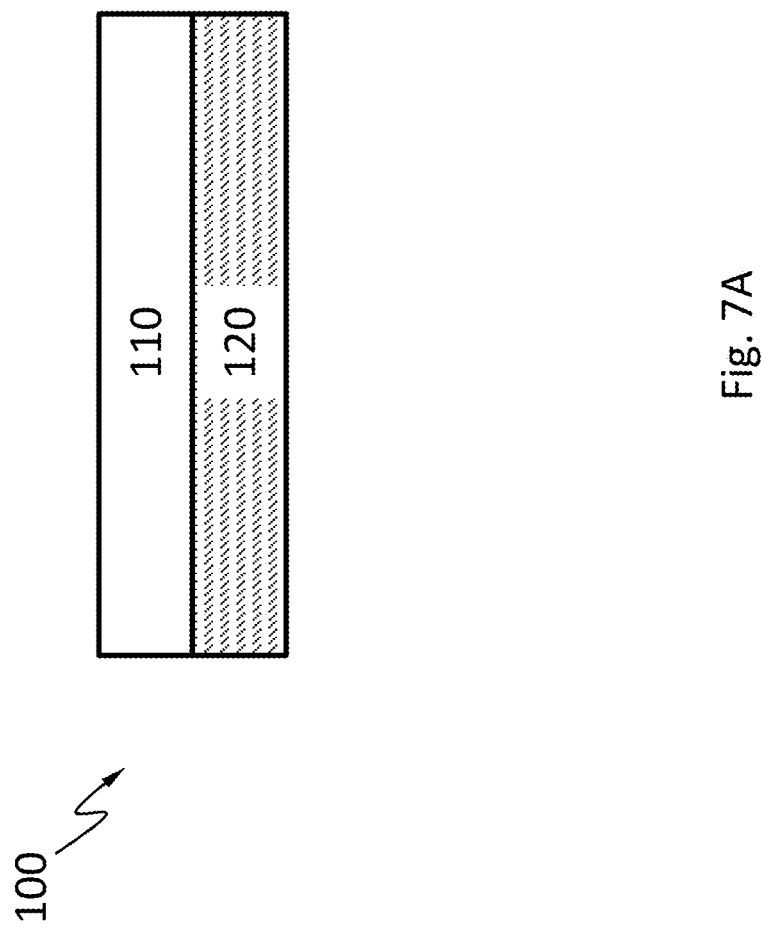
FIG. 7A schematically shows a cross-sectional view of a radiation detector, according to an embodiment.

FIG. 7A schematically shows a cross-sectional view of one radiation detector 100, according to an embodiment. The radiation detector 100 may include a radiation absorption layer 110 and an electronics layer 120 (e.g., an ASIC) for processing or analyzing electrical signals incident radiation generates in the radiation absorption layer 110. In an embodiment, the radiation detector 100 does not comprise a scintillator. The radiation absorption layer 110 may include a semiconductor material such as, silicon, germanium, GaAs, CdTe, CdZnTe, or a combination thereof. The semiconductor may have a high mass attenuation coefficient for the radiation energy of interest.

Figure 7B:
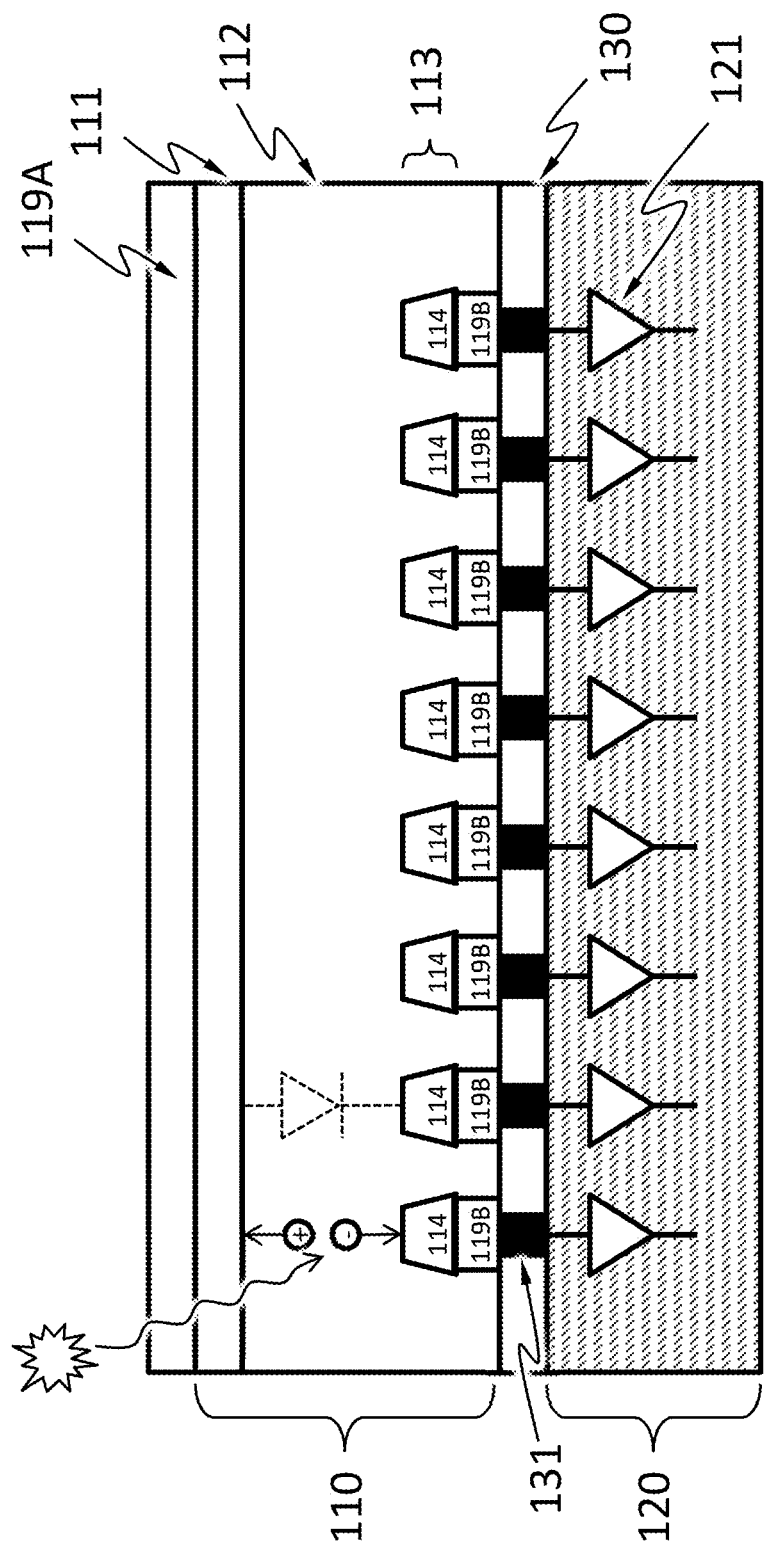
FIG. 7B schematically shows a detailed cross-sectional view of the radiation detector, according to an embodiment.

As shown in a detailed cross-sectional view of the radiation detector 100 in FIG. 7B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 7B, each of the discrete regions 114 of the second doped region 113 forms a diode with the first doped region 111 and the optional intrinsic region 112. Namely, in the example in FIG. 7B, the radiation absorption layer 110 has a plurality of diodes having the first doped region 111 as a shared electrode. The first doped region 111 may also have discrete portions.

When a particle of radiation hits the radiation absorption layer 110 including diodes, the particle of radiation may be absorbed and generate one or more charge carriers by a number of mechanisms. A particle of radiation may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single particle of radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of radiation incident around the footprint of one of these discrete regions 114 are not substantially shared with another of these discrete regions 114. The pixel 150 associated with a discrete region 114 may be an area around the discrete region 114 in which substantially all (more than 98%, more than 99.5%, more than 99.9%, or more than 99.99% of) charge carriers generated by a particle of radiation incident therein flow to the discrete region 114. Namely, less than 2%, less than 1%, less than 0.1%, or less than 0.01% of these charge carriers flow beyond the pixel.

Figure 7C:
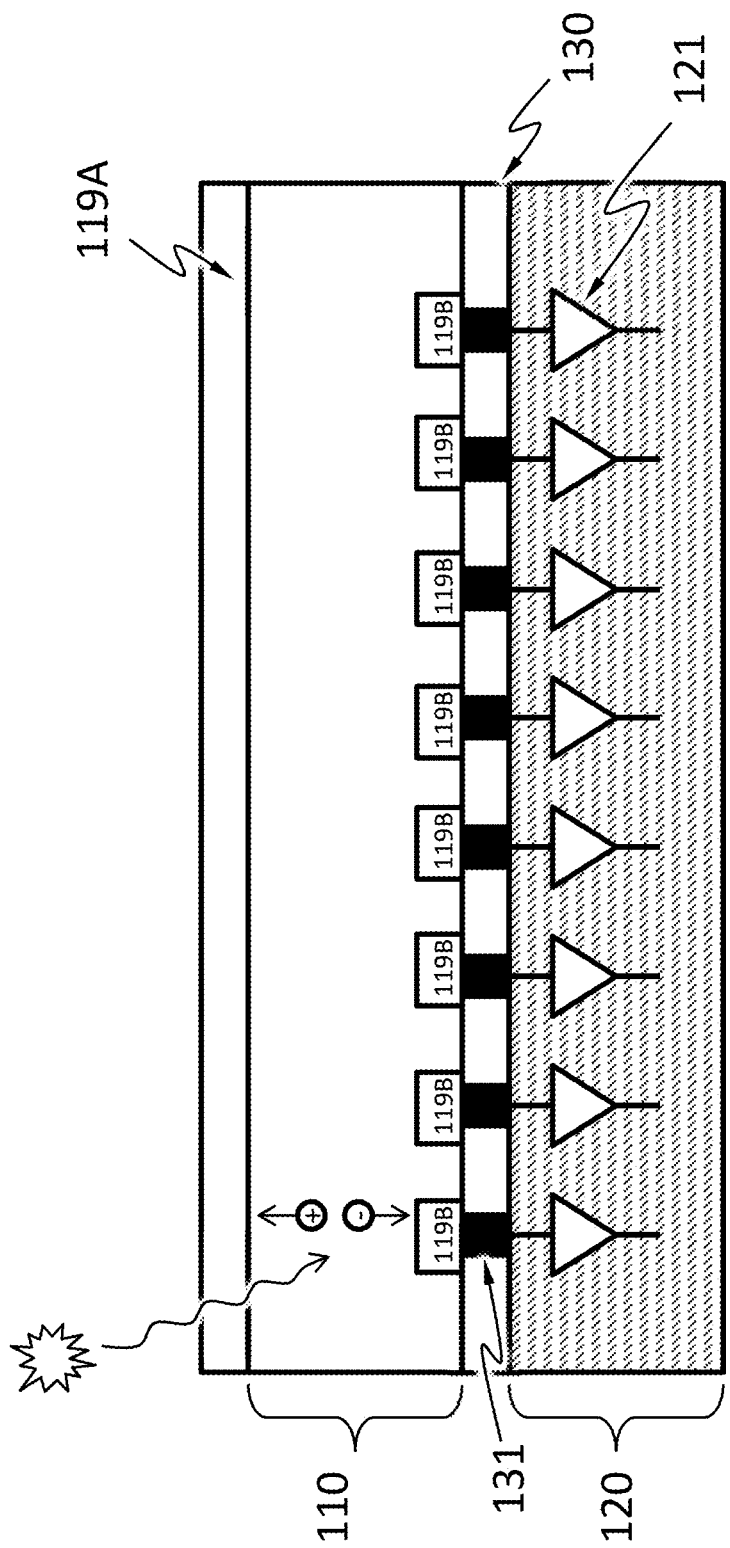
FIG. 7C schematically shows an alternative detailed cross-sectional view of the radiation detector, according to an embodiment.

As shown in an alternative detailed cross-sectional view of the detector 100 in FIG. 7C, according to an embodiment, the radiation absorption layer 110 may include a resistor of a semiconductor material such as, silicon, germanium, GaAs, CdTe, CdZnTe, or a combination thereof, but does not include a diode. The semiconductor may have a high mass attenuation coefficient for the radiation energy of interest.

When a particle of radiation hits the radiation absorption layer 110 including a resistor but not diodes, it may be absorbed and generate one or more charge carriers by a number of mechanisms. A particle of radiation may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single particle of radiation are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of radiation incident around the footprint of one of these discrete portions of the electrical contact 119B are not substantially shared with another of these discrete portions of the electrical contact 199B. The pixel 150 associated with a discrete portion of the electrical contact 119B may be an area around the discrete portion in which substantially all (more than 98%, more than 99.5%, more than 99.9% or more than 99.99% of) charge carriers generated by a particle of radiation incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 199B.

The electronics layer 120 may include an electronic system 121 suitable for processing or interpreting signals generated by particles of radiation incident on the radiation absorption layer 110. The electronic system 121 may include an analog circuitry such as a filter network, amplifiers, integrators, and comparators, or a digital circuitry such as a microprocessor, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

Figure 8:
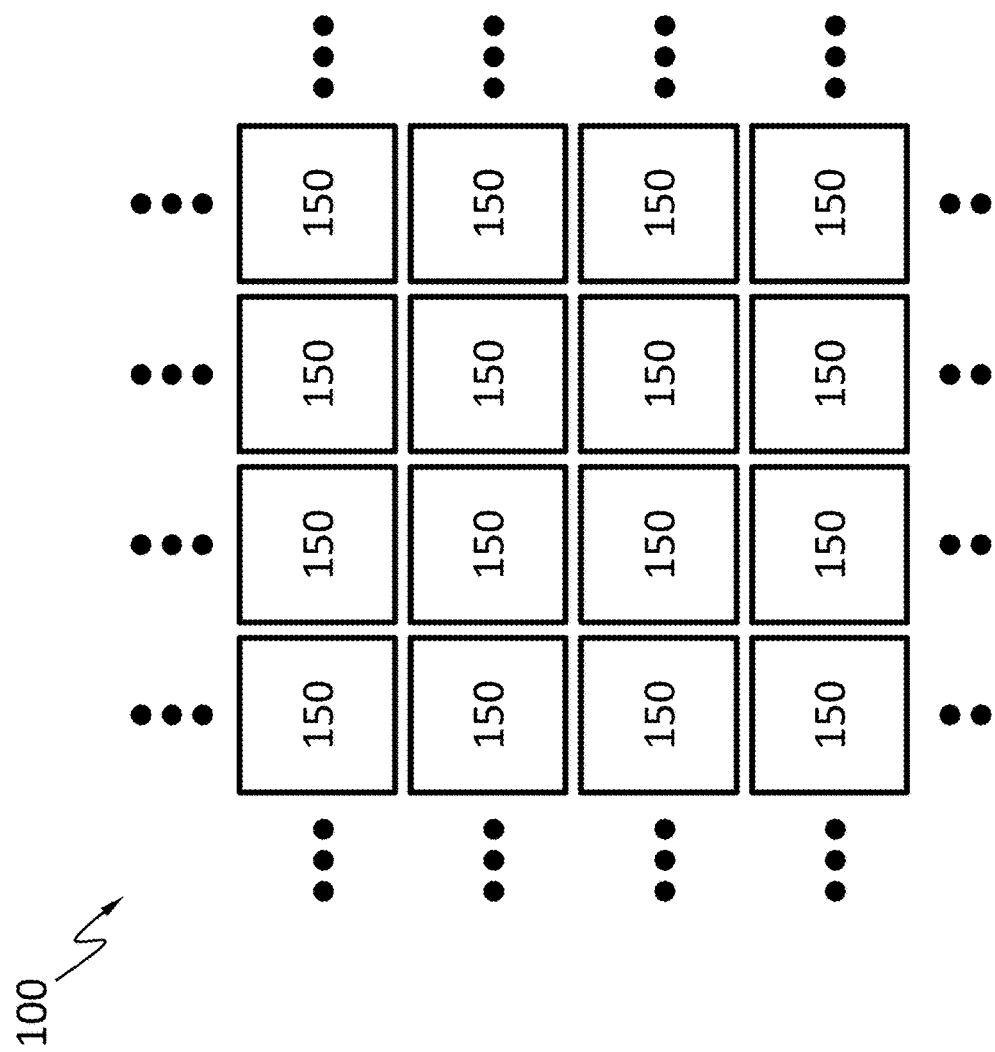
FIG. 8 schematically shows that the radiation detector may have an array of pixels, according to an embodiment.

FIG. 8 schematically shows that the radiation detector 100 may have an array of pixels 150. The array may be a rectangular array, a honeycomb array, a hexagonal array or any other suitable array. Each pixel 150 may be configured to detect a particle of radiation incident thereon, measure the energy of the particle of radiation, or both. For example, each pixel 150 may be configured to count numbers of particles of radiation incident thereon whose energy falls in a plurality of bins, within a period of time. All the pixels 150 may be configured to count the numbers of particles of radiation incident thereon within a plurality of bins of energy within the same period of time. Each pixel 150 may have its own analog-to-digital converter (ADC) configured to digitize an analog signal representing the energy of an incident particle of radiation into a digital signal. The ADC may have a resolution of 10 bits or higher. Each pixel 150 may be configured to measure its dark current, such as before or concurrently with each particle of radiation incident thereon. Each pixel 150 may be configured to deduct the contribution of the dark current from the energy of the particle of radiation incident thereon. The pixels 150 may be configured to operate in parallel. For example, when one pixel 150 measures an incident particle of radiation, another pixel 150 may be waiting for a particle of radiation to arrive. The pixels 150 may be but do not have to be individually addressable.

The image sensor 9000 described above may be used in various system such as those provided below.

Figure 9:
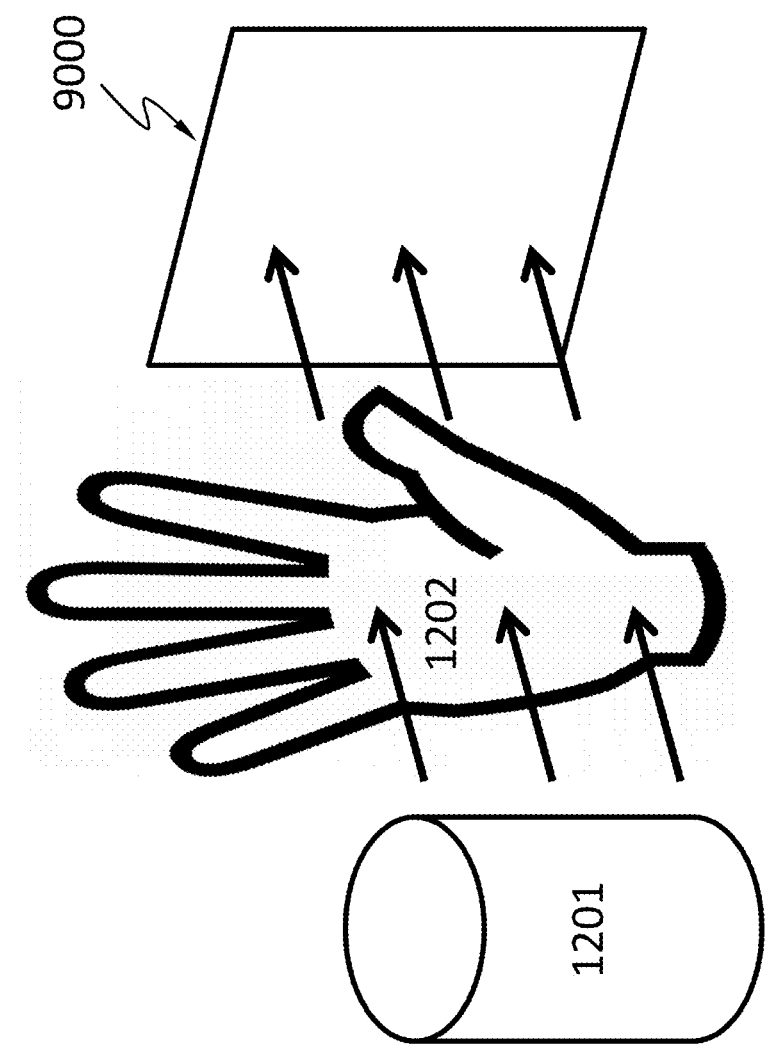
FIG. 9 schematically shows a system comprising the image sensor described herein, suitable for medical imaging such as chest radiography, abdominal radiography, etc., according to an embodiment.

FIG. 9 schematically shows a system comprising the image sensor 9000 as described herein. The system may be used for medical imaging such as chest radiation radiography, abdominal radiation radiography, etc. The system comprises a radiation source 1201. Radiation emitted from the radiation source 1201 penetrates an object 1202 (e.g., a human body part such as chest, limb, abdomen), is attenuated by different degrees by the internal structures of the object 1202 (e.g., bones, muscle, fat and organs, etc.), and is projected to the image sensor 9000. The image sensor 9000 forms an image by detecting the intensity distribution of the radiation.

Figure 10:
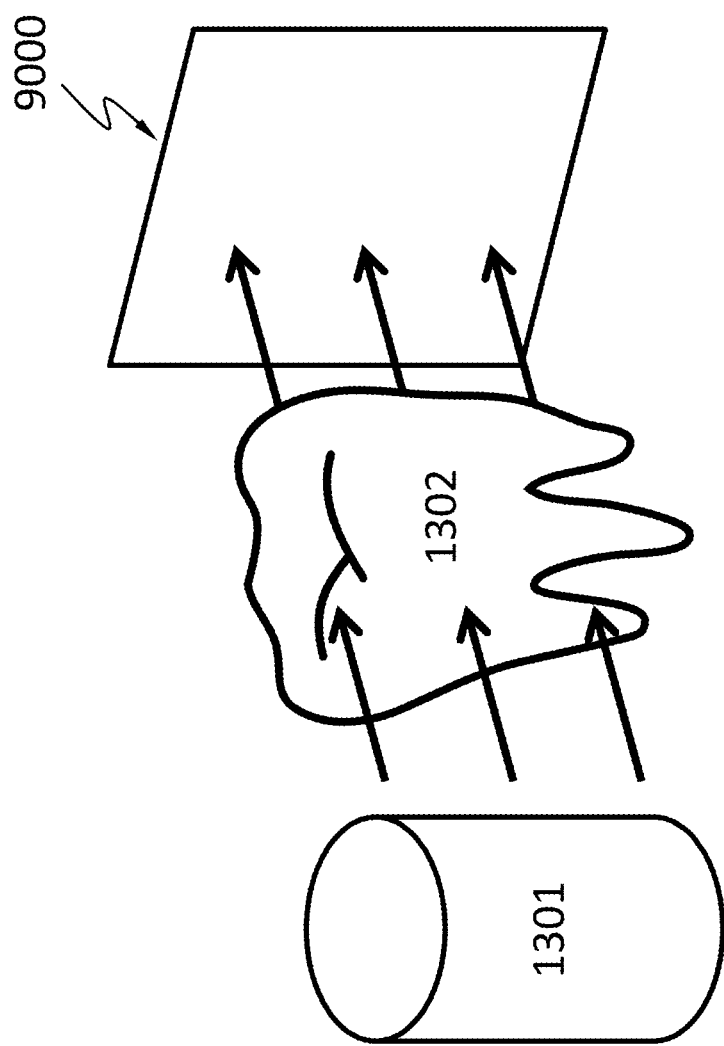
FIG. 10 schematically shows a system comprising the image sensor described herein suitable for dental radiography, according to an embodiment.

FIG. 10 schematically shows a system comprising the image sensor 9000 as described herein. The system may be used for medical imaging such as dental radiation radiography. The system comprises a radiation source 1301. Radiation emitted from the radiation source 1301 penetrates an object 1302 that is part of a mammal (e.g., human) mouth. The object 1302 may include a maxilla bone, a palate bone, a tooth, the mandible, or the tongue. The radiation is attenuated by different degrees by the different structures of the object 1302 and is projected to the image sensor 9000. The image sensor 9000 forms an image by detecting the intensity distribution of the radiation. Teeth absorb radiation more than dental caries, infections, periodontal ligament. The dosage of radiation received by a dental patient is typically small (around 0.150 mSv for a full mouth series).

Figure 11:
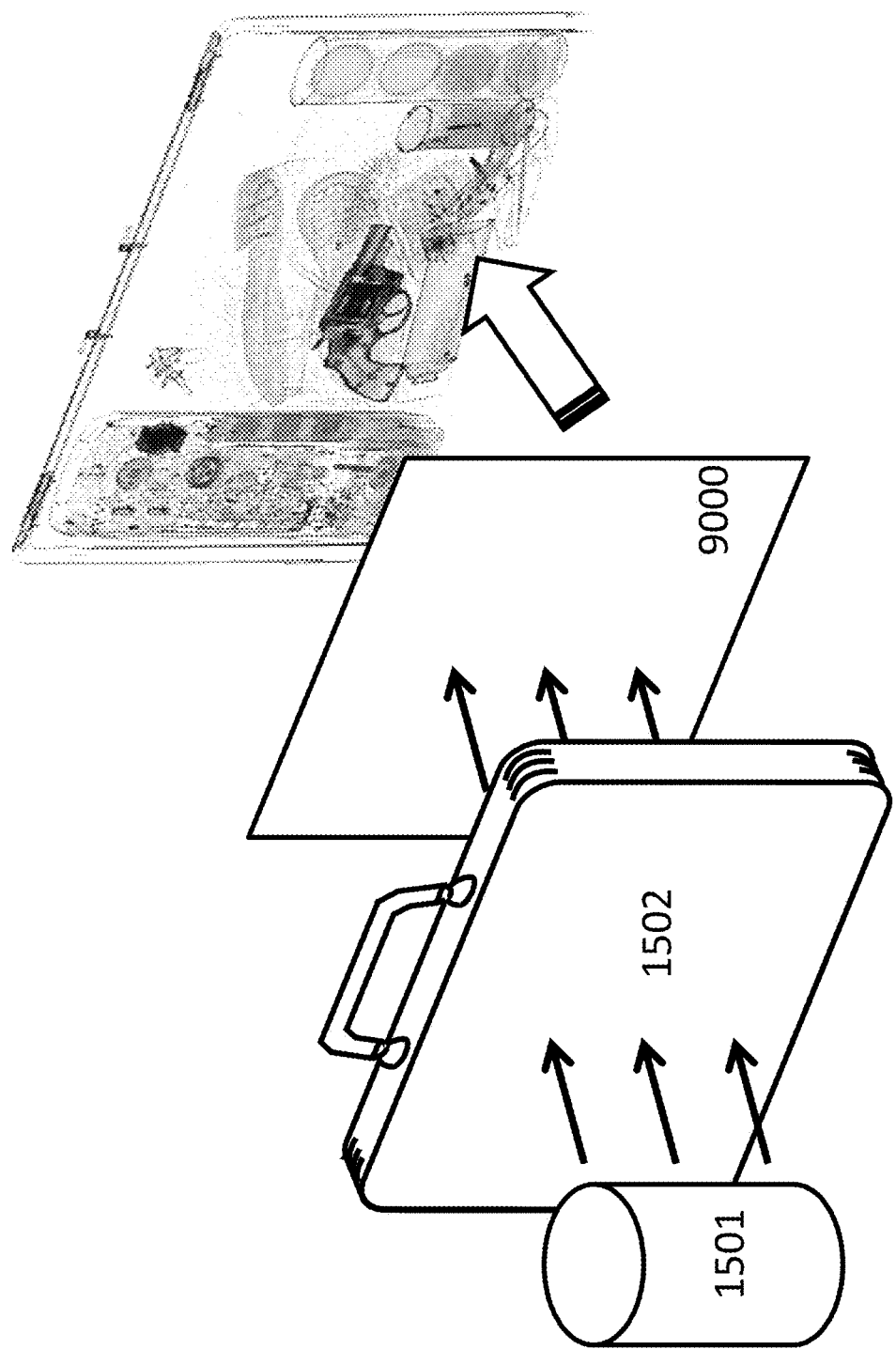
FIG. 11 schematically shows a cargo scanning or non-intrusive inspection (NII) system comprising the image sensor described herein, according to an embodiment.

FIG. 11 schematically shows a cargo scanning or non-intrusive inspection (NII) system comprising the image sensor 9000 as described herein. The system may be used for luggage screening at public transportation stations and airports. The system comprises a radiation source 1501. radiation emitted from the radiation source 1501 may penetrate a piece of luggage 1502, be differently attenuated by the contents of the luggage, and projected to the image sensor 9000. The image sensor 9000 forms an image by detecting the intensity distribution of the transmitted radiation. The system may reveal contents of luggage and identify items forbidden on public transportation, such as firearms, narcotics, edged weapons, flammables.

Figure 12:
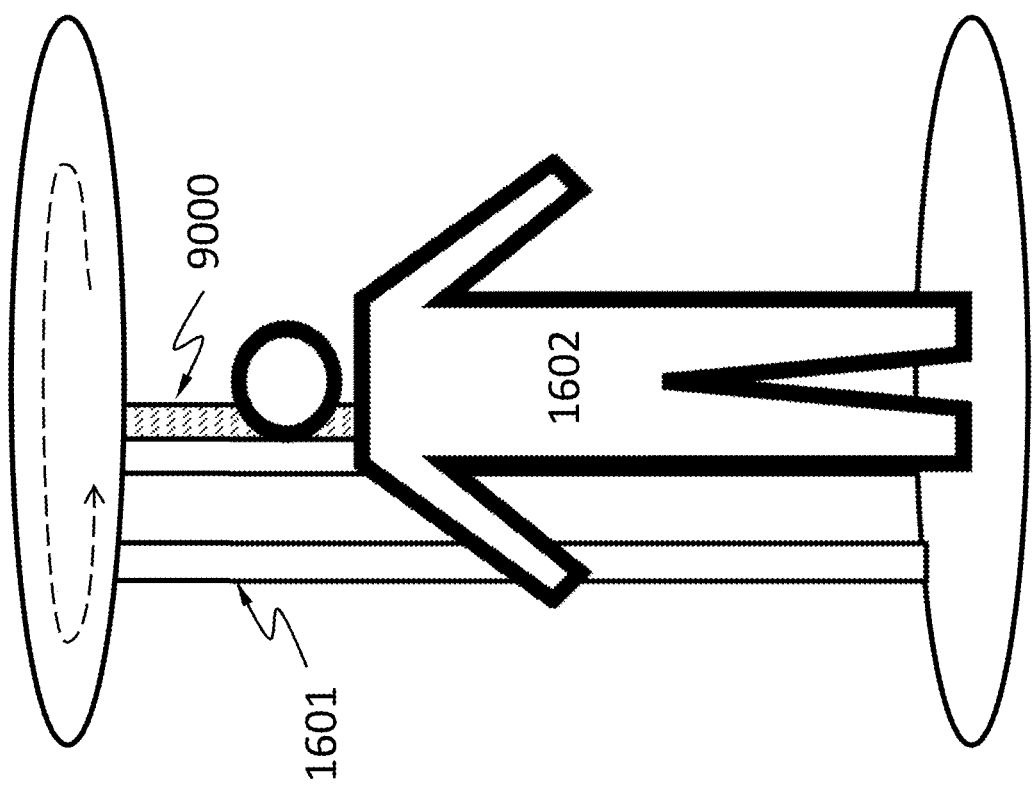
FIG. 12 schematically shows a full-body scanner system comprising the image sensor described herein, according to an embodiment.

FIG. 12 schematically shows a full-body scanner system comprising the image sensor 9000 as described herein. The full-body scanner system may detect objects on a person's body for security screening purposes, without physically removing clothes or making physical contact. The full-body scanner system may be able to detect non-metal objects. The full-body scanner system comprises a radiation source 1601. Radiation emitted from the radiation source 1601 may backscatter from a human 1602 being screened and objects thereon, and be projected to the image sensor 9000. The objects and the human body may backscatter radiation differently. The image sensor 9000 forms an image by detecting the intensity distribution of the backscattered radiation. The image sensor 9000 and the radiation source 1601 may be configured to scan the human in a linear or rotational direction.

Figure 13:
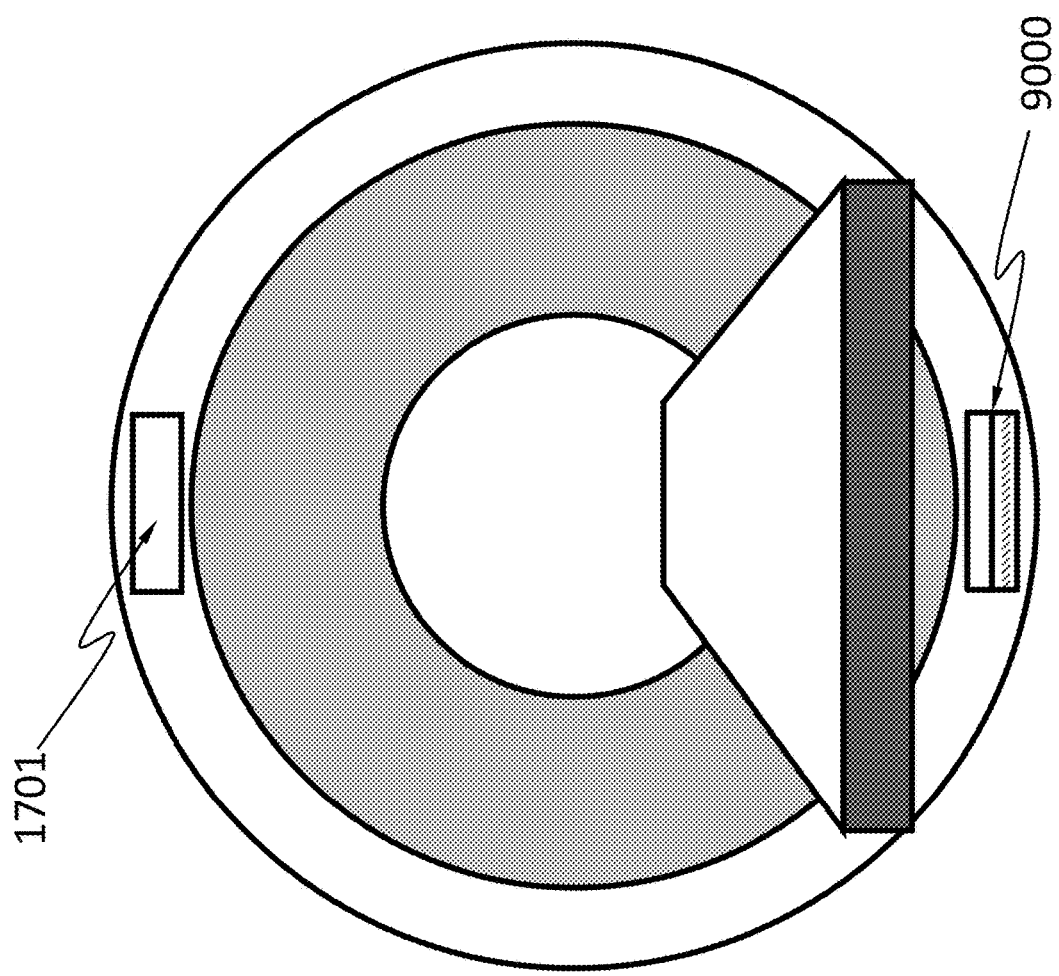
FIG. 13 schematically shows a radiation computed tomography (Radiation CT) system comprising the image sensor described herein, according to an embodiment.

FIG. 13 schematically shows a radiation computed tomography (Radiation CT) system. The radiation CT system uses computer-processed radiations to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The radiation CT system comprises the radiation detector 100 described herein and a radiation source 1701. The radiation detector 100 and the radiation source 1701 may be configured to rotate synchronously along one or more circular or spiral paths.

Figure 14:
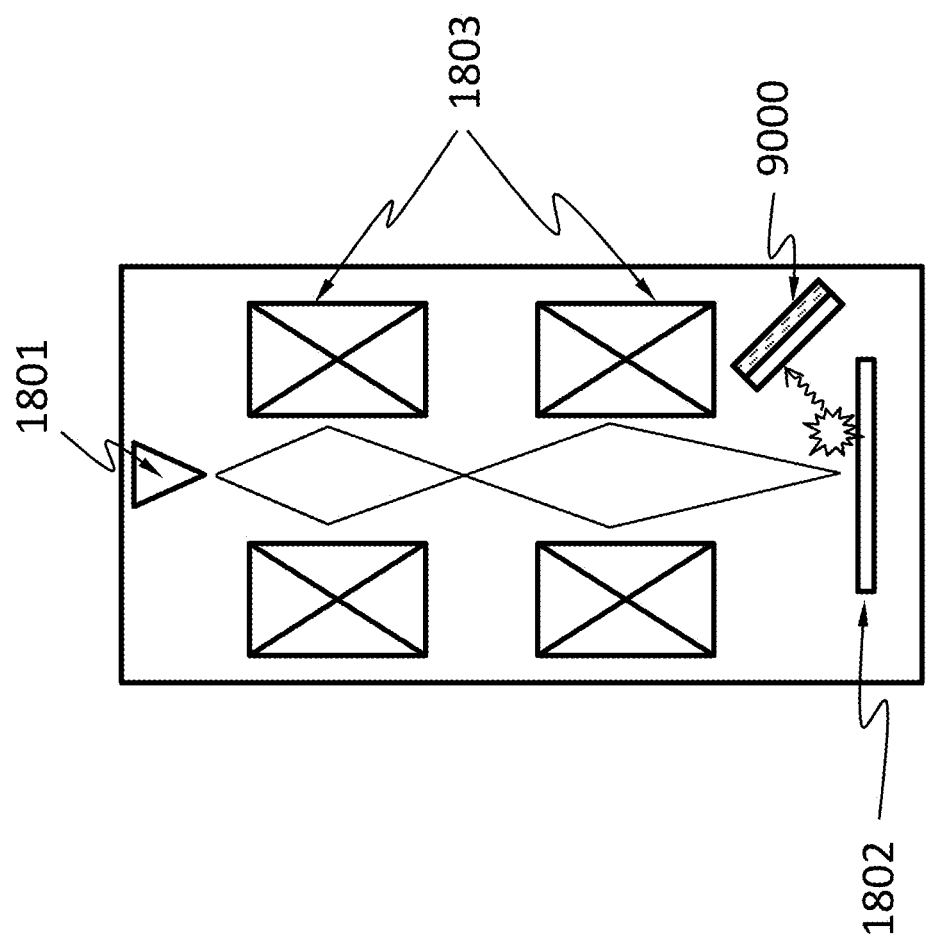
FIG. 14 schematically shows an electron microscope comprising the image sensor described herein, according to an embodiment.

FIG. 14 schematically shows an electron microscope. The electron microscope comprises an electron source 1801 (also called an electron gun) that is configured to emit electrons. The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the image sensor 9000 as described herein, for performing energy-dispersive radiation spectroscopy (EDS). EDS is an analytical technique used for the elemental analysis or chemical characterization of a sample. When the electrons incident on a sample, they cause emission of characteristic radiations from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of a radiation. The number and energy of the particles of radiation emitted from the sample can be measured by the image sensor 9000.

The image sensor 9000 described here may have other applications such as in a radiation telescope, or a radiation microscopy, or wherein the image sensor 9000 is configured to perform mammography, industrial defect detection, microscopy or microradiography, casting inspection, non-destructive testing, weld inspection, or digital subtraction angiography, etc. It may be suitable to use this image sensor 9000 in place of a photographic plate, a photographic film, a PSP plate, a radiation image intensifier, a scintillator, or another semiconductor radiation detector.

The electronics layer 120 in the radiation detector 100 may include an electronic system 121 suitable for processing or interpreting or correcting signals generated by particles of radiation incident on the pixels 150 comprising radiation absorption layer 110. The electronic system 121 may include an analog circuitry such as a filter network, amplifiers, integrators, and comparators, or a digital circuitry such as a microprocessor, and a memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

Figure 15A:
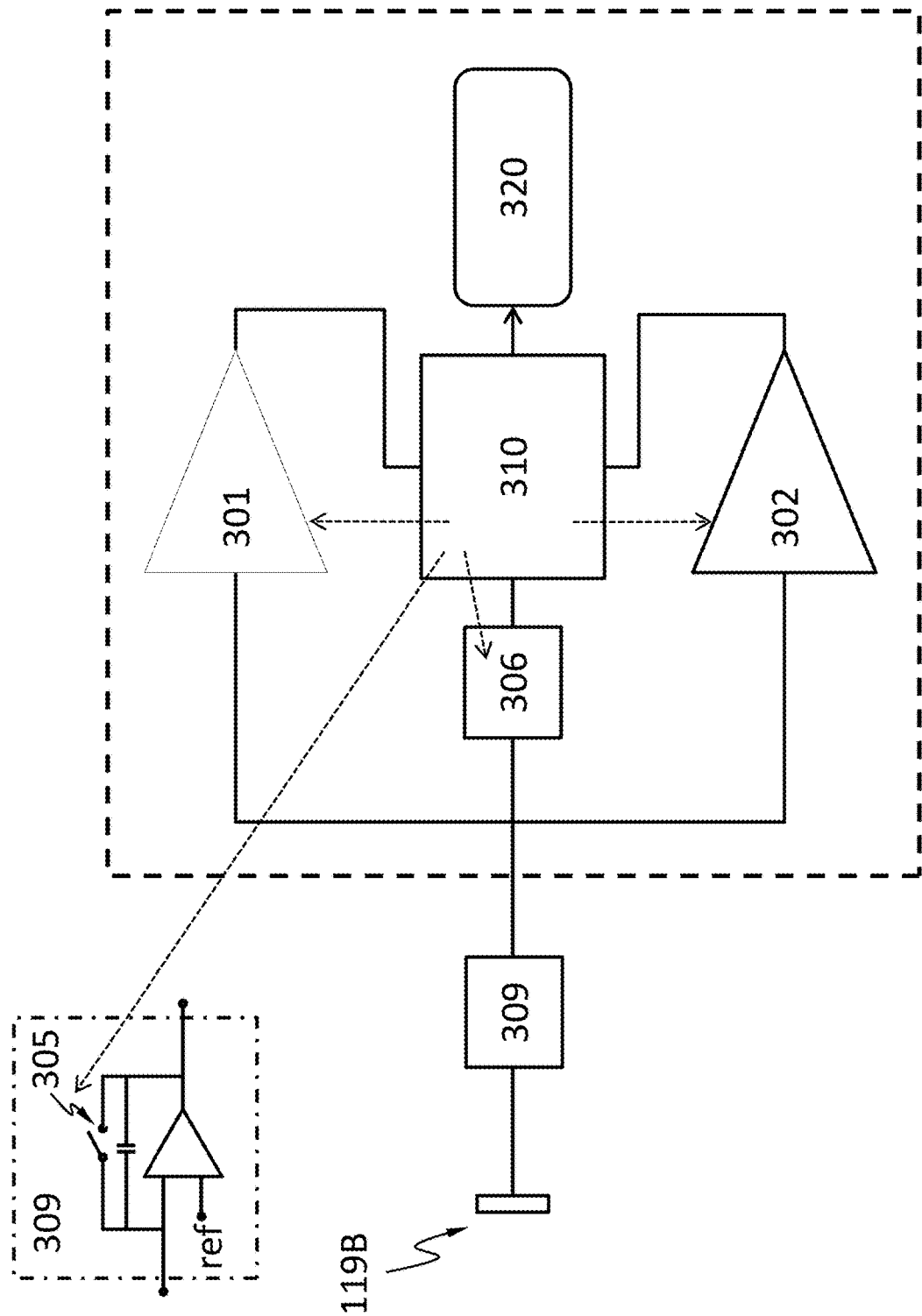
FIG. 15A and FIG. 15B each show a component diagram of an electronic system of the detector in FIG. 7A, FIG. 7B and FIG. 7C, according to an embodiment.
Figure 15B:
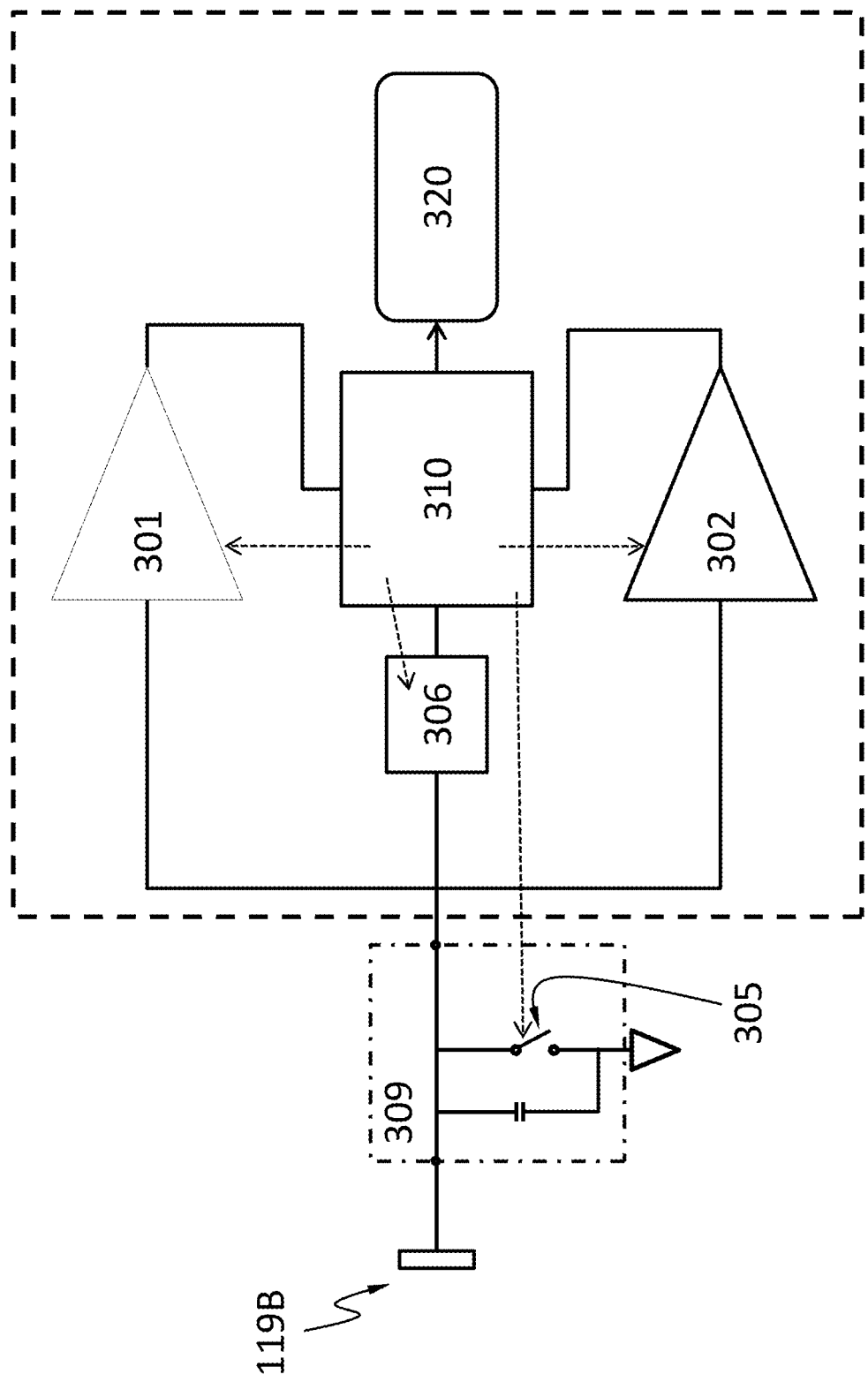

FIG. 15A and FIG. 15B each show a component diagram of the electronic system 121, according to an embodiment. The electronic system 121 may include a first voltage comparator 301, a second voltage comparator 302, a counter 320, a switch 305, an optional voltmeter 306, and a controller 310.

The first voltage comparator 301 is configured to compare the voltage of at least one of the electric contacts 119B to a first threshold. The first voltage comparator 301 may be configured to monitor the voltage directly or calculate the voltage by integrating an electric current flowing through the electrical contact 119B over a period of time. The first voltage comparator 301 may be controllably activated or deactivated by the controller 310. The first voltage comparator 301 may be a continuous comparator. Namely, the first voltage comparator 301 may be configured to be activated continuously and monitor the voltage continuously. The first voltage comparator 301 may be a clocked comparator. The first threshold may be 5-10%, 10%-20%, 20-30%, 30-40% or 40-50% of the maximum voltage one incident particle of radiation may generate on the electric contact 119B. The maximum voltage may depend on the energy of the incident particle of radiation, the material of the radiation absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, & \text{if } x \geq 0 \\ -x, & \text{if } x \leq 0 \end{cases}.$$

The second threshold may be 200%-300% of the first threshold. The second threshold may be at least 50% of the maximum voltage one incident particle of radiation may generate on the electric contact 119B. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident particles of radiation. However, having a high speed is often at the cost of power consumption.

The counter 320 is configured to register at least a number of particles of radiation incident on the pixel 150 encompassing the electric contact 119B. The counter 320 may be a software component (e.g., a number stored in a computer memory) or a hardware component (e.g., a 4017 IC and a 7490 IC).

The controller 310 may be a hardware component such as a microcontroller or a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause at least one of the number registered by the counter 320 to increase by one, if, during the time delay, the second voltage comparator 302 determines that the absolute value of the voltage equals or exceeds the absolute value of the second threshold.

The controller 310 may be configured to cause the optional voltmeter 306 to measure the voltage upon expiration of the time delay. The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

The electronic system 121 may include an integrator 309 electrically connected to the electric contact 119B, wherein the integrator is configured to collect charge carriers from the electric contact 119B. The integrator 309 can include a capacitor in the feedback path of an amplifier. The amplifier configured as such is called a capacitive transimpedance amplifier (CTIA). CTIA has high dynamic range by keeping the amplifier from saturating and improves the signal-tonoise ratio by limiting the bandwidth in the signal path. Charge carriers from the electric contact 119B accumulate on the capacitor over a period of time ("integration period"). After the integration period has expired, the capacitor voltage is sampled and then reset by a reset switch. The integrator 309 can include a capacitor directly connected to the electric contact 119B.

Figure 16:
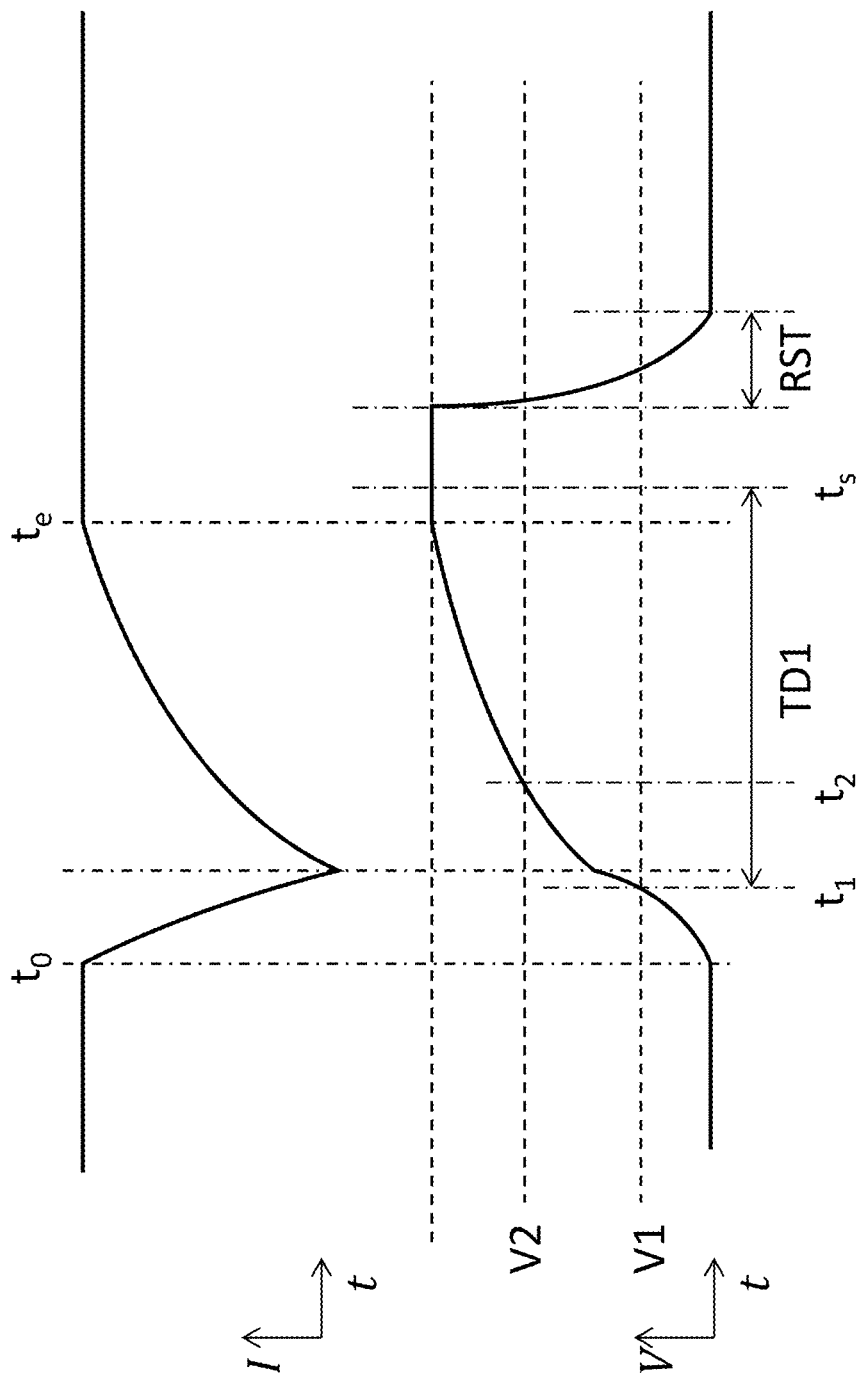
FIG. 16 schematically shows a temporal change of the electric current flowing through an electrode (upper curve) of a diode or an electrical contact of a resistor of a radiation absorption layer exposed to radiation, the electric current caused by charge carriers generated by a particle of radiation incident on the radiation absorption layer, and a corresponding temporal change of the voltage of the electrode (lower curve), according to an embodiment.

FIG. 16 schematically shows a temporal change of the electric current flowing through the electric contact 119B (upper curve) caused by charge carriers generated by a particle of radiation incident on the pixel 150 encompassing the electric contact 119B, and a corresponding temporal change of the voltage of the electric contact 119B (lower curve). The voltage may be an integral of the electric current with respect to time. At time to, the particle of radiation hits pixel 150, charge carriers start being generated in the pixel 150, electric current starts to flow through the electric contact 119B, and the absolute value of the voltage of the electric contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold V2 at time $t_2$, the controller 310 waits for stabilization of the voltage to stabilize. The voltage stabilizes at time $t_e$, when all charge carriers generated by the particle of radiation drift out of the radiation absorption layer 110. At time $t_s$, the time delay TD1 expires. At or after time $t_e$, the controller 310 causes the voltmeter 306 to digitize the voltage and determines which bin the energy of the particle of radiation falls in. The controller 310 then causes the number registered by the counter 320 corresponding to the bin to increase by one. In the example of FIG. 16, time $t_s$ is after time $t_e$; namely TD1 expires after all charge carriers generated by the particle of radiation drift out of the radiation absorption layer 110. If time $t_e$ cannot be easily measured, TD1 can be empirically chosen to allow sufficient time to collect essentially all charge carriers generated by a particle of radiation but not too long to risk have another incident particle of radiation. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the particle of radiation, which relates to the energy of the particle of radiation. The controller 310 may be configured to determine the energy of the particle of radiation, using the voltmeter 306.

After TD1 expires or digitization by the voltmeter 306, whichever later, the controller 310 connects the electric contact 119B to an electric ground for a reset period RST to allow charge carriers accumulated on the electric contact 119B to flow to the ground and reset the voltage. After RST, the system 121 is ready to detect another incident particle of radiation. If the first voltage comparator 301 has been deactivated, the controller 310 can activate it at any time before RST expires. If the controller 310 has been deactivated, it may be activated before RST expires.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An image sensor comprising:
   a plurality of radiation detectors;
   a mask with a plurality of radiation transmitting zones and a radiation blocking zone; and
   an actuator configured to move the plurality of radiation detectors from a first position to a second position and to move the mask from a third position to a fourth position;
   wherein while the radiation detectors are at the first position and the mask is at the third position and while the radiation detectors are at the second position and the mask is at the fourth position, the radiation blocking zone blocks radiation from a radiation source that would otherwise incident on a dead zone of the image sensor and the radiation transmitting zones allow at least a portion of radiation from the radiation source that would incident on active areas of the image sensor to pass through.

2. The image sensor of claim 1, wherein the image sensor is configured to capture, by using the radiation detectors, an image of a first portion of a scene when the radiation detectors are at the first position and the image sensor is configure to capture, by using the radiation detectors, an image of a second portion of a scene when the radiation detectors are at the second position, wherein the image sensor is configured to form an image of the scene by stitching the image of the first portion and the image of the second portion.

3. The image sensor of claim 1, wherein the plurality of radiation detectors are spaced apart.

4. The image sensor of claim 1, further comprising a shutter configured to block the radiation from the radiation source during movement of the radiation detectors.

5. The image sensor of claim 1, wherein the actuator comprises a first linear motor and a second linear motor;
   wherein the first linear motor is configured to move the radiation detectors from the first position to the second position;
   wherein the second linear motor is configured to move the mask from the third position to the fourth position.

6. The image sensor of claim 1, wherein the actuator comprises a third linear motor and a linkage;
   wherein the third linear motor is configured to move radiation detectors from the first position to the second position;
   wherein the linkage couples the mask to the radiation detectors such that movement of the radiation detectors from the first position to the second position causes the mask to move from the third position to the fourth position.

7. The image sensor of claim 1, wherein the actuator comprises a third linear motor and a linkage;
   wherein the third linear motor is configured to move the mask to from the third position to the fourth position;

wherein the linkage couples the radiation detectors to the mask such that movement of the mask from the third position to the fourth position causes the radiation detectors to move from the first position to the second position.

8. The image sensor of claim 1, wherein the actuator comprises a third linear motor and a linkage;
wherein the third linear motor is configured to drive the linkage;
wherein the linkage causes the mask to move from the third position to the fourth position and causes the radiation detectors to move from the first position to the second position.

9. The image sensor of claim 1, wherein the actuator comprises a step motor and a transmission;
wherein the step motor is configured to move radiation detectors from the first position to the second position and to drive the transmission;
wherein the transmission is configured to move the mask from the third position to the fourth position.

10. The image sensor of claim 1, wherein at least some of the plurality of radiation detectors are arranged in staggered rows.

11. The image sensor of claim 1, wherein radiation detectors in a same row are uniform in size; wherein a distance between two neighboring radiation detectors in a same row is greater than a width of one radiation detector in the same row in an extending direction of the row and is less than twice that width.

12. The image sensor of claim 2, wherein active areas of the radiation detectors tessellate the scene at the positions.

13. The image sensor of claim 1, wherein at least some of the plurality of radiation detectors comprise multiple layers of detectors.

14. The image sensor of claim 1, wherein at least some of the plurality of radiation detectors are rectangular in shape.

15. The image sensor of claim 1, wherein at least some of the plurality of radiation detectors are hexagonal in shape.

16. The image sensor of claim 1, wherein at least one of the plurality of radiation detectors comprises a radiation absorption layer and an electronics layer;
wherein the radiation absorption layer comprises an electrode;
wherein the electronics layer comprises an electronics system;
wherein the electronics system comprises:
a first voltage comparator configured to compare a voltage of the electrode to a first threshold,
a second voltage comparator configured to compare the voltage to a second threshold,
a counter configured to register a number of particles of radiation reaching the radiation absorption layer, and
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the number registered by the counter to increase by one, if the second voltage comparator determines that an absolute value of the voltage equals or exceeds an absolute value of the second threshold.

17. The image sensor of claim 16, wherein the electronics system further comprises a capacitor module electrically connected to the electrode, wherein the capacitor module is configured to collect charge carriers from the electrode.

18. The image sensor of claim 16, wherein the controller is configured to activate the second voltage comparator at a beginning or expiration of the time delay.

19. The image sensor of claim 16, wherein the electronics system further comprises a voltmeter, wherein the controller is configured to cause the voltmeter to measure the voltage upon expiration of the time delay.

20. The image sensor of claim 16, wherein the controller is configured to determine energy of a particle of radiation based on a value of the voltage measured upon expiration of the time delay.

21. The image sensor of claim 16, wherein the controller is configured to connect the electrode to an electrical ground.

22. The image sensor of claim 16, wherein a rate of change of the voltage is substantially zero at expiration of the time delay.

23. The image sensor of claim 16, wherein a rate of change of the voltage is substantially non-zero at expiration of the time delay.

24. A system comprising the image sensor of claim 1 and a radiation source, wherein the system is configured to perform radiography on human chest or abdomen.

25. A system comprising the image sensor of claim 1 and a radiation source, wherein the system is configured to perform radiography on human mouth.

26. A cargo scanning or non-intrusive inspection (NII) system, comprising the image sensor of claim 1 and a radiation source, wherein the cargo scanning or non-intrusive inspection (NII) system is configured to form an image using radiation transmitted through an object inspected.

27. A full-body scanner system comprising the image sensor of claim 1 and a radiation source.

28. A radiation computed tomography (radiation CT) system comprising the image sensor of claim 1 and a radiation source.

29. An electron microscope comprising the image sensor of claim 1, an electron source and an electronic optical system.

30. A system comprising the image sensor of claim 1, wherein the system is a radiation telescope, or a radiation microscopy, or wherein the system is configured to perform mammography, industrial defect detection, microradiography, casting inspection, weld inspection, or digital subtraction angiography.

* * * * *